(12) United States Patent
Landis et al.

(10) Patent No.: US 7,892,228 B2
(45) Date of Patent: *Feb. 22, 2011

(54) DUAL MODE LESION FORMATION APPARATUS, SYSTEMS AND METHODS

(75) Inventors: William G. Landis, San Jose, CA (US); Greg Eberl, Sunnyvale, CA (US); David K. Swanson, Campbell, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1363 days.

This patent is subject to a terminal disclaimer.

(21) Appl. No.: 11/110,149

(22) Filed: Apr. 20, 2005

(65) Prior Publication Data

US 2006/0195081 A1 Aug. 31, 2006

Related U.S. Application Data

(63) Continuation-in-part of application No. 11/067,535, filed on Feb. 25, 2005.

(51) Int. Cl.
*A61B 18/18* (2006.01)
(52) U.S. Cl. .......................... 606/41; 606/51
(58) Field of Classification Search .............. 606/41, 606/49, 50–52
See application file for complete search history.

(56) References Cited

U.S. PATENT DOCUMENTS

| | | | |
|---|---|---|---|
| 4,011,872 A | 3/1977 | Komiya | |
| 4,685,459 A | 8/1987 | Koch et al. | |
| 5,190,541 A * | 3/1993 | Abele et al. | 606/46 |
| 5,342,359 A | 8/1994 | Rydell | |
| 5,364,395 A * | 11/1994 | West, Jr. | 606/46 |
| 5,398,683 A | 3/1995 | Edwards | |
| 5,443,463 A | 8/1995 | Stern | |
| 5,450,846 A | 9/1995 | Goldreyer | |
| 5,484,435 A | 1/1996 | Fleenor | |
| 5,545,193 A | 8/1996 | Fleischman | |
| 5,582,609 A | 12/1996 | Swanson | |
| 5,637,090 A | 6/1997 | McGee | |

(Continued)

FOREIGN PATENT DOCUMENTS

DE 4116970 A1 11/1992

(Continued)

OTHER PUBLICATIONS

PCT International Search Report dated May 31, 2006 for Int. App. No. PCT/US2006/003268.

(Continued)

*Primary Examiner*—Thomas J Sweet
*Assistant Examiner*—Jaymi Della
(74) *Attorney, Agent, or Firm*—Vista IP Law Group LLP

(57) ABSTRACT

A dual mode lesion formation apparatus and associated methods. A dual mode lesion formation apparatus may include a probe component having an energy transmission element carried on a shaft, a clamp component mountable on the clamp member and including a temperature sensor, a first electrical connector and a second electrical connector. The first electrical connector is operably connected to a probe component energy transmission element. The second electrical connector is operably connected to a probe component energy transmission element and to a clamp component temperature sensor.

30 Claims, 10 Drawing Sheets

U.S. PATENT DOCUMENTS

| | | | |
|---|---|---|---|
| 5,673,695 A | 10/1997 | McGee | |
| 5,697,882 A | 12/1997 | Eggers | |
| 5,755,760 A | 5/1998 | Maguire et al. | |
| 5,776,130 A | 7/1998 | Buysse | |
| 5,782,899 A | 7/1998 | Imran | |
| 5,788,688 A | 8/1998 | Bauer | |
| 5,797,905 A | 8/1998 | Fleischman | |
| 5,824,005 A | 10/1998 | Motamedi | |
| 5,871,523 A | 2/1999 | Fleischman | |
| 5,904,681 A * | 5/1999 | West, Jr. | 606/41 |
| 5,931,811 A | 8/1999 | Haissaguerre et al. | |
| 5,938,694 A | 8/1999 | Jaraczewski | |
| 5,944,718 A | 8/1999 | Austin | |
| 5,971,983 A | 10/1999 | Lesh | |
| 5,980,519 A | 11/1999 | Hahnen et al. | |
| 6,004,269 A | 12/1999 | Crowley | |
| 6,010,500 A | 1/2000 | Sherman | |
| 6,013,052 A | 1/2000 | Durman et al. | |
| 6,023,638 A | 2/2000 | Swanson | |
| 6,050,996 A | 4/2000 | Schmaltz et al. | |
| 6,056,747 A | 5/2000 | Saadat | |
| 6,063,080 A | 5/2000 | Nelson et al. | |
| 6,096,037 A | 8/2000 | Mulier et al. | |
| 6,113,596 A | 9/2000 | Hooven | |
| 6,115,626 A | 9/2000 | Whayne | |
| 6,142,994 A | 11/2000 | Swanson | |
| 6,171,305 B1 | 1/2001 | Sherman | |
| 6,183,468 B1 | 2/2001 | Swanson | |
| 6,190,381 B1 | 2/2001 | Olsen et al. | |
| 6,203,525 B1 | 3/2001 | Whayne | |
| 6,214,002 B1 | 4/2001 | Fleischman et al. | |
| 6,224,593 B1 * | 5/2001 | Ryan et al. | 606/41 |
| 6,237,605 B1 * | 5/2001 | Vaska et al. | 128/898 |
| 6,241,754 B1 | 6/2001 | Swanson et al. | |
| 6,245,068 B1 | 6/2001 | Olson et al. | |
| 6,277,117 B1 * | 8/2001 | Tetzlaff et al. | 606/48 |
| 6,286,512 B1 | 9/2001 | Loeb et al. | |
| 6,308,104 B1 | 10/2001 | Taylor | |
| 6,311,692 B1 | 11/2001 | Vaska | |
| 6,314,962 B1 | 11/2001 | Vaska | |
| 6,319,249 B1 | 11/2001 | Tollner | |
| 6,325,797 B1 | 12/2001 | Stewart | |
| 6,464,700 B1 | 10/2002 | Koblish | |
| 6,468,272 B1 | 10/2002 | Koblish | |
| 6,471,699 B1 | 10/2002 | Fleischman | |
| 6,522,905 B2 | 2/2003 | Desai | |
| 6,522,930 B1 | 2/2003 | Schaer et al. | |
| 6,529,756 B1 | 3/2003 | Phan | |
| 6,542,773 B2 | 4/2003 | Dupree et al. | |
| 6,542,781 B1 | 4/2003 | Koblish | |
| 6,544,262 B2 | 4/2003 | Fleischman | |
| 6,558,408 B1 * | 5/2003 | Fogarty et al. | 606/207 |
| 6,584,360 B2 | 6/2003 | Francischelli | |
| 6,616,661 B2 * | 9/2003 | Wellman et al. | 606/50 |
| 6,645,200 B1 | 11/2003 | Koblish et al. | |
| 6,645,202 B1 | 11/2003 | Pless | |
| 6,692,491 B1 * | 2/2004 | Phan | 606/41 |
| 6,699,240 B2 * | 3/2004 | Francischelli | 606/32 |
| 6,706,038 B2 | 3/2004 | Francischelli | |
| 6,771,996 B2 | 8/2004 | Bowe | |
| 6,807,968 B2 | 10/2004 | Francischelli | |
| 6,889,694 B2 | 5/2005 | Hooven | |
| 7,250,048 B2 | 7/2007 | Francischelli et al. | |
| 2001/0012918 A1 | 8/2001 | Swanson | |
| 2001/0025177 A1 | 9/2001 | Woloszko et al. | |
| 2002/0002372 A1 | 1/2002 | Jahns | |
| 2002/0120267 A1 * | 8/2002 | Phan | 606/51 |
| 2003/0014048 A1 | 1/2003 | Swanson | |
| 2003/0078644 A1 | 4/2003 | Phan | |
| 2003/0097126 A1 | 5/2003 | Woloszko et al. | |
| 2003/0158547 A1 | 8/2003 | Phan | |
| 2003/0158549 A1 | 8/2003 | Swanson | |
| 2003/0212444 A1 | 11/2003 | Truckai et al. | |
| 2004/0059325 A1 | 3/2004 | Swanson | |
| 2004/0097117 A1 | 5/2004 | Gonnering | |
| 2004/0106937 A1 * | 6/2004 | Berube et al. | 606/151 |
| 2004/0186467 A1 | 9/2004 | Swanson | |
| 2005/0119648 A1 | 6/2005 | Swanson | |
| 2005/0119649 A1 | 6/2005 | Swanson | |
| 2005/0119653 A1 | 6/2005 | Swanson | |
| 2005/0119654 A1 | 6/2005 | Swanson | |
| 2005/0187544 A1 | 8/2005 | Swanson | |
| 2005/0203499 A1 | 9/2005 | Pendekanti et al. | |
| 2006/0047277 A1 * | 3/2006 | Eberl et al. | 606/41 |
| 2006/0100619 A1 | 5/2006 | McClurken | |
| 2006/0155274 A1 | 7/2006 | Swanson et al. | |
| 2006/0195080 A1 | 8/2006 | Ebert | |
| 2006/0195081 A1 | 8/2006 | Landis et al. | |

FOREIGN PATENT DOCUMENTS

| | | |
|---|---|---|
| EP | 0 694 291 A1 | 1/1996 |
| EP | 1125549 A2 | 8/2001 |
| EP | 1 557 129 A1 | 7/2005 |
| WO | WO 01/72234 A1 | 10/2001 |

OTHER PUBLICATIONS

EPO Communication issued Mar. 18, 2008 for EP Patent Application No. 03756823.5 (now EP Patent No. 1542604), with Letter of Opposition from Hoffman Eitle dated Mar. 11, 2008 (6 pages).
Prosecution History for U.S. Appl. No. 10/930,073 including: Amendment dated Jan. 28, 2008 for U.S. Appl. No. 10/930,073 (15 pages). Non Final Office Action dated Sep. 27, 2007 for U.S. Appl. No. 10/930,073 (8 pages). Amendment dated Aug. 23, 2007 for U.S. Appl. No. 10/930,073 (15 pages). Final Office Action dated Jun. 21, 2007 for U.S. Appl. No. 10/930,073 (11 pages). Amendment dated Apr. 27, 2007 for U.S. Appl. No. 10/930,073 (14 pages). Non-Final Office Action dated Mar. 2, 2007 for U.S. Appl. No. 10/930,073 (6 pages).
PCT International Search Report dated Dec. 1, 2005 for PCT/US2005/028515 (6 pages).
PCT Written Opinion dated Dec. 1, 2005 for PCT/US2005/028515 (5 pages).
PCT International Preliminary Report on Patentability dated Mar. 8, 2007 for PCT/US2005/028515 (7 pages).
Prosecution History for U.S. Appl. No. 10/727,143 including: Amendment dated Oct. 15, 2007 for U.S. Appl. No. 10/727,143, filed Dec. 2, 2003 (13 pages). Non-Final Office Action dated Jun. 15, 2007 for U.S. Appl. No. 10/727,143, filed Dec. 2, 2003 (9 pages). Amendment dated Apr. 26, 2007 for U.S. Appl. No. 10/727,143, filed Dec. 2, 2003 (12 pages) Final Office Action dated Feb. 1, 2007 for U.S. Appl. No. 10/727,143, filed Dec. 2, 2003 (8 pages). Amendment dated Nov. 22, 2006 for U.S. Appl. No. 10/727,143, filed Dec. 2, 2003 (12 pages) Non-Final Office Action dated Aug. 18, 2006 for U.S. Appl. No. 10/727,143, filed Dec. 2, 2003 (8 pages).
PCT International Search Report dated Apr. 7, 2005 for PCT Application No. PCT/US2004/039282, Applicant Boston Scientific Scimed, form PCT/ISA 210, (4 pages).
PCT Written Opinion dated Jun. 2, 2006, for International Application No. PCT/US2004/39282 (7 pages).
PCT International Preliminary Examination Report on Patentability dated Jun. 7, 2006 for PCT/US2004/39282 (8 pages).
Prosecution History for U.S. Appl. No. 11/131,671, filed May 17, 2005 including: Notice of Allowance dated Jan. 9, 2008 for U.S. Appl. No. 11/131,671, filed May 17, 2005 (5 pages) Notice of Allowance dated Aug. 22, 2007 for U.S. Appl. No. 11/131,671, filed May 17, 2005 (6 pages) Notice of Allowance dated May 10, 2007 for U.S. Appl. No. 11/131,671, filed May 17, 2005 (7 pages) Amendment dated Feb. 14, 2007 for U.S. Appl. No. 11/131,671, filed May 17, 2005 (11 pages) Non-Final Office Action dated Jun. 30, 2006 for U.S. Appl. No. 11/131,671, filed May 17, 2005 (12 pages) Advisory Action dated May 24, 2006 for U.S. Appl. No. 11/131,671, filed May 17, 2005 (3 pages) Amendment dated May 4, 2006 for U.S. Appl. No. 11/131,671, filed May 17, 2005 (12 pages) Final Office Action dated Feb. 27, 2006 for U.S. Appl. No. 11/131,671, filed May 17, 2005 (10 pages) Amendment dated Dec. 2, 2005 for U.S. Appl. No. 11/131,671, filed May 17, 2005 (14 pages) Non-Final Office Action dated Sep. 26, 2005 for U.S. Appl. No. 11/131,671, filed May 17, 2005 (9 pages).

Prosecution History for for U.S. Appl. No. 10/255, filed Sep. 24, 2002 including: Amendment dated Jan. 24, 2008 for U.S. Appl. No. 10/255,025, filed Sep. 24, 2002 (16 pages). Non final Office Action dated Sep. 24, 2007 for US U.S. Appl. No. 10/255,025, filed Sep. 24, 2002 (7 pages). Notice of Allowance dated May 10, 2006 for U.S. Appl. No. 10/255,025, filed Sep. 24, 2002 (4 pages). Amendment dated Apr. 28, 2006 for U.S. Appl. No. 10/255,025, filed Sep. 24, 2002 (8 pages). Final Office Action dated Feb. 14, 2006 for U.S. Appl. No. 10/255,025, filed Sep. 24, 2002 (11 pages). Amendment dated Dec. 3, 2005 for U.S. Appl. No. 10/255,025, filed Sep. 24, 2002 (19 pages). Declaration of Dr. David K. Swanson Under §132 dated Nov. 22, 2005 for U.S. Appl. No. 10/255,025, filed Sep. 24, 2002 (3 pages). Non-Final Office Action dated Jul. 13, 2005 for U.S. Appl. No. 10/255,025, filed Sep. 24, 2002 (9 pages). Advisory Action dated Apr. 11, 2005 for U.S. Appl. No. 10/255,025, filed Sep. 24, 2002 (2 pages). Amendment dated Mar. 14, 2005 for U.S. Appl. No. 10/255,025, filed Sep. 24, 2002 (20 pages). Final Office Action dated Dec. 7, 2004 for US U.S. Appl. No. 10/255,025, filed Sep. 24, 2002 (10 pages). Amendment dated Sep. 28, 2004 for U.S. Appl. No. 10/255,025, filed Sep. 24, 2002 (16 pages). Non-Final Office Action dated Jul. 19, 2004 for U.S. Appl. No. 10/255,025, filed Sep. 24, 2002 (8 pages).

International Search Report for PCT/US2003/29270, dated Jan. 12, 2004, forms PCT/ISA 210 and 220, Applicant Boston Scientific Scimed, (10 pages).

Communication under Rule 51(4) EPC, dated Aug. 8, 2005, for EP application No. 03756823.5, Applicant Boston Scientific Scimed, (6 pages).

Communication of a Notice of Opposition, dated Nov. 29, 2006, for EP application No. 03756823.5, Applicant Boston Scientific Scimed, (15 pages).

Response to Notice of Opposition for EP application No. 03756823.5, dated Jun. 19, 2007, Applicant Boston Scientific Scimed, (8 pages).

Prosecution History for U.S. Appl. No.10/368,108, filed Feb. 14, 2003 including: Notice of Allowance dated Nov. 16, 2007 for U.S. Appl. No. 10/368,108 (6 pages) Amendment Response dated Oct. 16, 2007 for U.S. Appl. No. 10/368,108 (16 pages) Non-Final Office Action dated Jun. 19, 2007 for U.S. Appl. No. 10/368,108 (6 pages) Response dated Nov. 22, 2006 for U.S. Appl. No. 10/368,108 (10 pages) Non-Final Office Action dated Aug. 28, 2006 for U.S. Appl. No. 10/368,108 (4 pages) Response dated Jun. 1, 2006 for U.S. Appl. No. 10/368,108 (10 pages). Non-Final Office Action dated Mar. 30, 2006 for U.S. Appl. No. 10/368,108 (5 pages) Response dated Nov. 11, 2005 for U.S. Appl. No. 10/368,108 (10 pages) Non-Final Office Action dated Jul. 18, 2005 for U.S. Appl. No. 10/368,108 (5 pages) Amendment dated Jun. 9, 2005 for U.S. Appl. No. 10/368,108 (16 pages). Final Office Action dated Apr. 15, 2005 for U.S. Appl. No. 10/368,108 (5 pages) Response dated Mar. 14, 2005 for U.S. Appl. No. 10/368,108 (10 pages) Final Office Action dated Dec. 14, 2004 for U.S. Appl. No. 10/368,108 (5 pages) Amendment dated Sep. 3, 2004 for U.S. Appl. No. 10/368,108 (16 pages) Non-Final Office Action dated Jul. 14, 2004 for U.S. Appl. No. 10/368,108 (5 pages).

PCT International Search Report dated Oct. 27, 2006 for PCT/US2005/045055 (10 pages).

International Search Report for (PCT/US02/38092), forms PCT/ISA 210 and 220, dated Mar. 28, 2003, Applicant Boston Scientific Scimed, (7 pages).

(Written Opinion for (PCT/US02/38092), Form PCT/IPEA 408,dated Nov. 13, 2003, Applicant Boston Scientific Scimed, (5 pages).

International Preliminary Examination Report for PCT/US02/38092, dated Mar. 12, 2004, Form PCT/IPEA 416, Applicant Boston Scientific Scimed, (7 pages).

PCT Written Opinion for PCT/US2006/03268 dated May 31, 2006, Applicant Boston Scientific Scimed, (5 pages).

PCT International Preliminary Report on Patentability for PCT/US2006/03268 dated Nov. 1, 2007, Applicant Boston Scientific Scimed, (7 pages).

Office Action dated Mar. 31, 2008 for related U.S. Appl. No. 10/255,025, filed Sep. 24, 2002, Inventor: David K. Swanson (10 pages).

Amendment dated Jun. 26, 2008 for related U.S. Appl. No. 10/255,025, filed Sep. 24, 2002, Inventor: David K. Swanson (23 pages).

Office Action dated Mar. 26, 2008 for related U.S. Appl. No. 11/031,629, filed Jan. 8, 2005, Inventor: David K. Swanson (16 pages).

Amendment dated Jun. 26, 2008 for related U.S. Appl. No. 11/031,629, filed Jan. 8, 2005, Inventor: David K. Swanson (17 pages).

Office Action dated Mar. 17, 2008 for related U.S. Appl. No. 10/930,073, filed Aug. 30, 2004, Inventor: Greg Eberl (7 pages).

Amendment dated May 15, 2008 for related U.S. Appl. No. 10/930,073, filed Aug. 30, 2004, Inventor: Greg Eberl (18 pages).

Office Action dated Jun. 4, 2008 for related U.S. Appl. No. 10/930,073, filed Aug. 30, 2004, Inventor: Greg Eberl (7 pages).

Office Action dated Mar. 27, 2008 for related U.S. Appl. No. 10/727,143, filed Dec. 2, 2003, Inventor: David K. Swanson (9 pages).

Amendment dated May 21, 2008 for related U.S. Appl. No. 10/727,143, filed Dec. 2, 2003, Inventor: David K. Swanson (17 pages).

Office Action dated Jun. 12, 2008 for related U.S. Appl. No. 10/727,143, filed Dec. 2, 2003, Inventor: David K. Swanson (9 pages).

Sep. 12, 2008 Amendment in U.S. Appl. No. 10/727,143.
Sep. 4, 2008 Amendment in U.S. Appl. No. 10/930,073.
Jul. 25, 2008 Office Action in U.S. Appl. No. 10/255,025.
Jul. 17, 2009 Office Action in U.S. Appl. No. 10/727,143 20 pgs.
Apr. 24, 2009 Amendment in U.S. Appl. No. 10/727,143 23 pgs.
Jan. 26, 2009 Office Action in U.S. Appl. No. 10/727,143 45 pgs.
Feb. 27, 2009 Notice of Allowance in U.S. Appl. No. 10/930,073 9 pgs.
Feb. 19, 2009 Amendment in U.S. Appl. No. 10/930,073 13 pgs.
Dec. 19, 2008 Office Action in U.S. Appl. No. 10/930,073 14 pgs.
May 21, 2009 Amendment in U.S. Appl. No. 10/255,025 13 pgs.
Mar. 24, 2009 Office Action in U.S. Appl. No. 10/255,025 19 pgs.
Oct. 22, 2008 Amendment in U.S. Appl. No. 10/255,025 24 pgs.
Aug. 6, 2009 Office Action in U.S. Appl. No. 11/031,629 11 pgs.
Jun. 30, 2009 Amendment in U.S. Appl. No. 11/031,629 19 pgs.
Apr. 30, 2009 Office Action in U.S. Appl. No. 11/031,629 12 pgs.
Mar. 13, 2009 Amendment in U.S. Appl. No. 11/031,629 14 pgs.
Nov. 14, 2008 Office Action in U.S. Appl. No. 11/031,629 32 pgs.

Amendment dated Jan. 12, 2010 for related U.S. Appl. No. 10/727,143, filed Dec. 2, 2003, Inventor: David K. Swanson (7 pages).

Office Action dated Apr. 30, 2010 for related U.S. Appl. No. 10/727,143, filed Dec. 2, 2003, Inventor: David K. Swanson (6 pages).

Advisory Action dated Jun. 1, 2009 for related U.S. Appl. No. 10/255,025, filed Sep. 24, 2002, Inventor: David K. Swanson (3 pages).

Notice of Allowance dated Oct. 1, 2009 for related U.S. Appl. No. 10/255,025, filed Sep. 24, 2002, Inventor: David K. Swanson (6 pages).

Amendment dated Nov. 10, 2009 for related U.S. Appl. No. 11/031,629, filed Jan. 8, 2005, Inventor: David K. Swanson (11 pages).

Notice of Allowance dated Jan. 27, 2010 for related U.S. Appl. No. 11/031,629, filed Jan. 8, 2005, Inventor: David K. Swanson (4 pages).

* cited by examiner

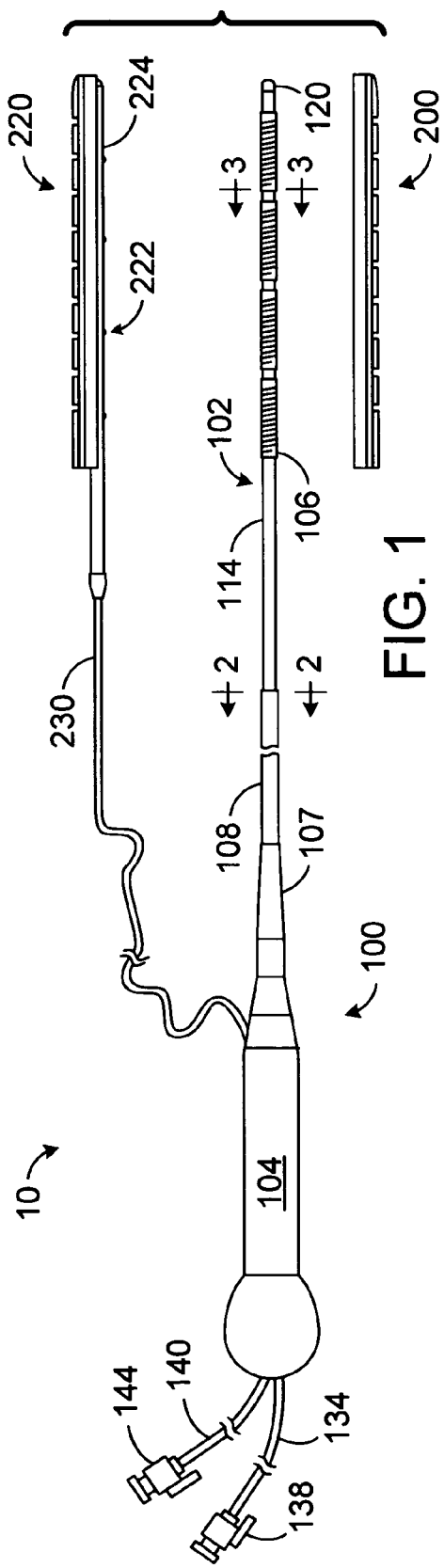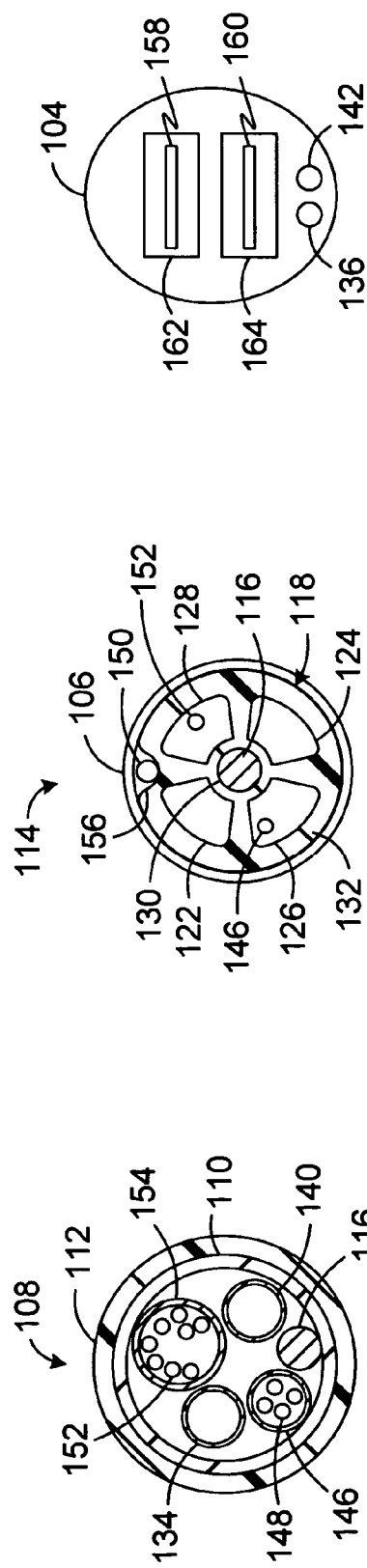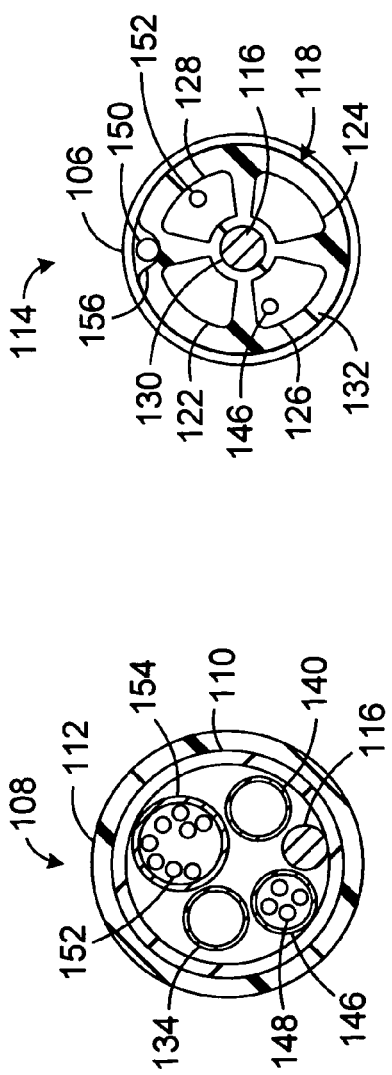

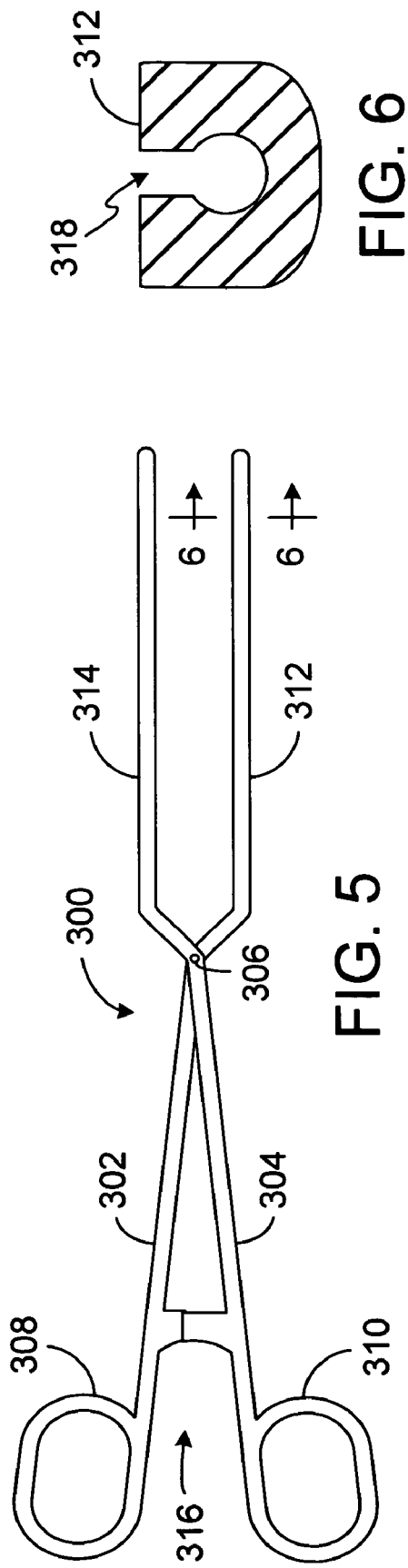

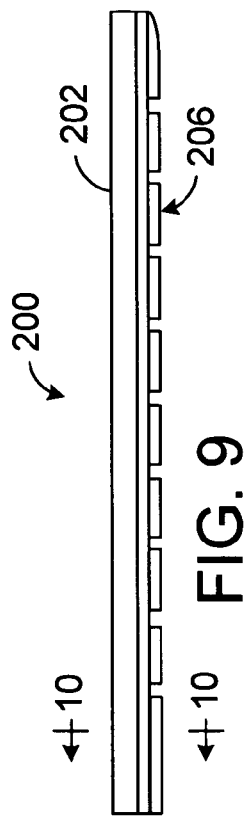
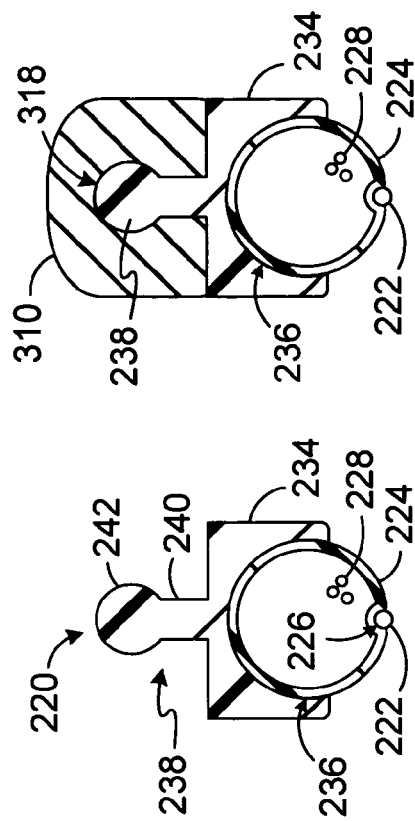
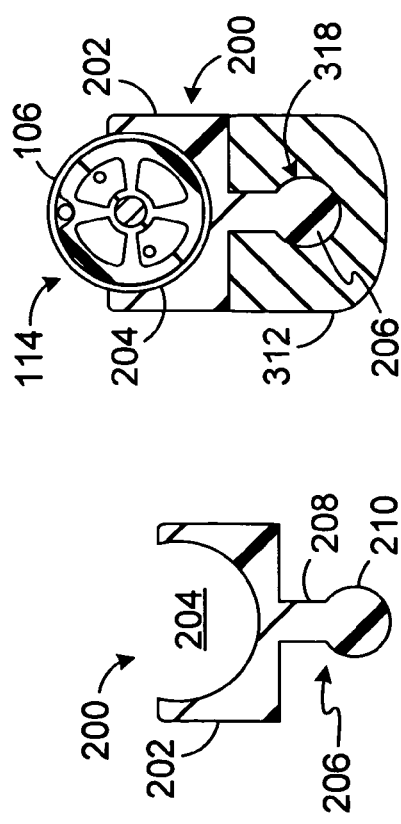
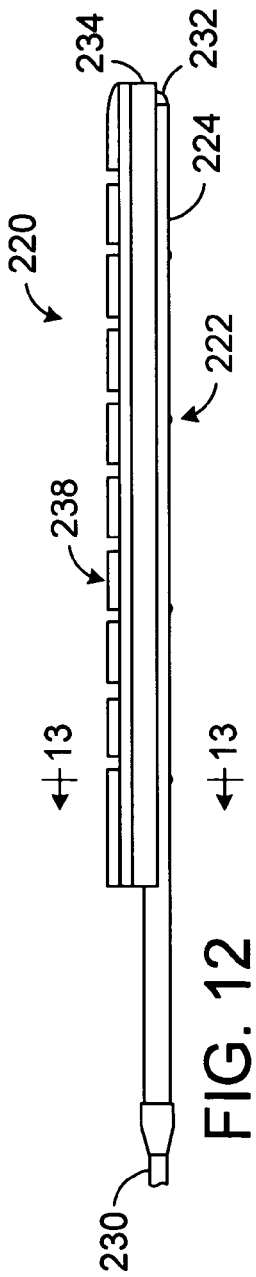

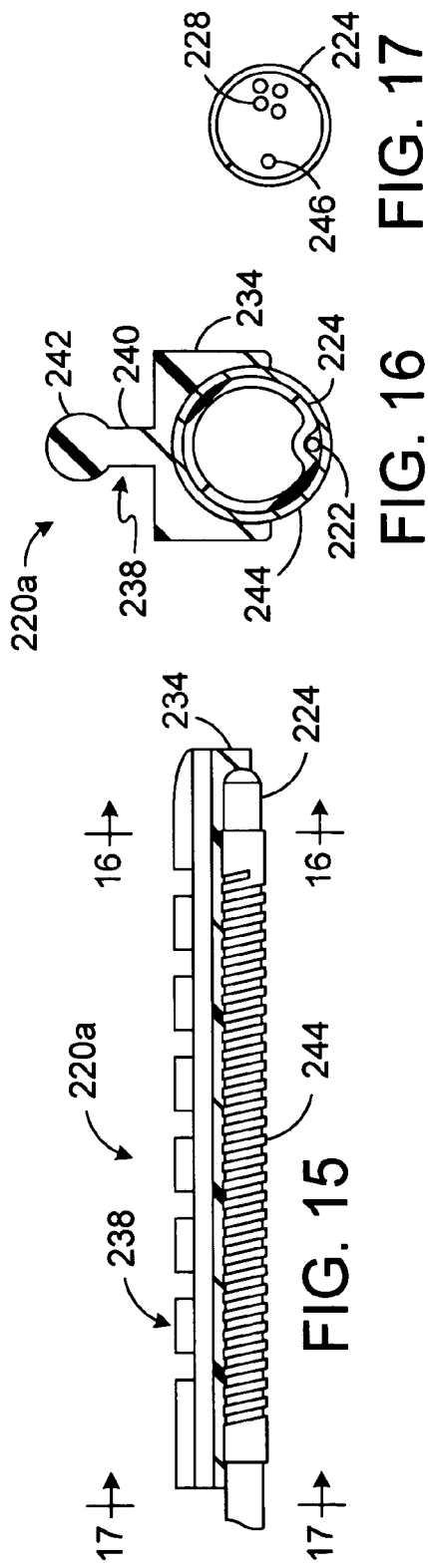
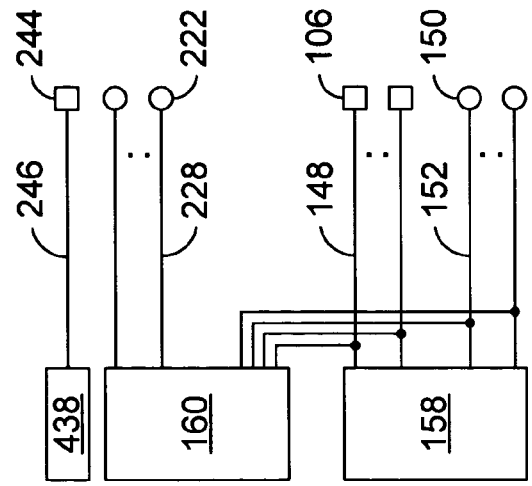

US 7,892,228 B2

DUAL MODE LESION FORMATION APPARATUS, SYSTEMS AND METHODS

CROSS-REFERENCE TO RELATED APPLICATIONS

This application is a continuation-in-part of co-pending U.S. application Ser. No. 11/067,535, filed Feb. 25, 2005, which is incorporated herein by reference.

BACKGROUND OF THE INVENTIONS

1. Field of Inventions

The present inventions relate generally to devices for performing therapeutic operations on body tissue.

2. Description of the Related Art

There are many instances where electrosurgical devices are used to form therapeutic lesions in tissue. Therapeutic lesions are frequently formed to treat conditions in the heart, prostate, liver, brain, gall bladder, uterus, breasts, lungs and other solid organs. Electromagnetic radio frequency ("RF") may, for example, be used to heat and eventually kill (i.e. "ablate") tissue to form a lesion. During the ablation of soft tissue (i.e. tissue other than blood, bone and connective tissue), tissue coagulation occurs and it is the coagulation that kills the tissue. Thus, references to the ablation of soft tissue are necessarily references to soft tissue coagulation. "Tissue coagulation" is the process of cross-linking proteins in tissue to cause the tissue to jell. In soft tissue, it is the fluid within the tissue cell membranes that jells to kill the cells, thereby killing the tissue.

The tissue coagulation energy is typically supplied by an electrosurgical unit ("ESU") during the therapeutic procedure. More specifically, after a catheter, surgical probe or clamp has been connected to the ESU, and the electrodes or other energy transmission elements on the catheter, surgical probe or clamp have been positioned adjacent to the target tissue, energy from the ESU is transmitted through the energy transmission elements to the tissue to from a lesion. The amount of power required to coagulate tissue ranges from 5 to 150 W.

Some electrosurgical procedures require the use of more than one electrosurgical device. One example of such a procedure involves the formation of therapeutic lesions to treat cardiac conditions such as atrial fibrillation. Here, a clamp may be used to create a first transmural epicardial lesion around the right pulmonary vein pair and a second transmural epicardial lesion around the left pulmonary vein pair. Thereafter, if needed, a surgical probe may be used to create a linear transmural epicardial lesion between the right and left pulmonary vein pairs. A linear transmural lesion that extends from the lesion between the right and left pulmonary vein pairs to the left atrial appendage may also be created.

The present inventors have determined that conventional lesion formation devices are susceptible to improvement. For example, the present inventors have determined that there may be more efficient and cost effective ways, in terms of materials, manufacturing, sterilization, shipping, etc., to provide physicians with the capabilities of two separate devices, such as the aforementioned separate clamp and surgical probe.

SUMMARY OF THE INVENTIONS

A dual mode apparatus in accordance with one invention herein includes a probe component, a clamp component configured to be mounted on a clamp member, a first electrical connector and a second electrical connector. The first electrical connector is operably connected to the probe component and the second electrical connector is operably connected to the probe component and to the clamp component. A system in accordance with a present invention includes the dual mode apparatus and a source of tissue coagulation and/or a clamp. A method of forming a lesion with the dual mode apparatus includes connecting one of the electrical connectors to a source of tissue coagulation energy and transmitting the tissue coagulation energy to the tissue with the probe component.

A method in accordance with a present invention includes supplying tissue coagulation energy to the first side of the tissue structure and discontinuing the supply of tissue coagulation energy to the first side of the tissue structure when a predetermined temperature is measured on the second side of the tissue structure.

BRIEF DESCRIPTION OF THE DRAWINGS

Detailed description of embodiments of the inventions will be made with reference to the accompanying drawings.

FIG. 1 is a plan view of a dual mode lesion formation apparatus in accordance with one embodiment of a present invention.

FIG. 2 is a section view taken along line 2-2 in FIG. 1.

FIG. 3 is a section view taken along line 3-3 in FIG. 1.

FIG. 4 is an end view of the handle illustrated in FIG. 1.

FIG. 5 is a plan view of a clamp in accordance with a preferred embodiment of a present invention.

FIG. 6 is a section view taken along line 6-6 in FIG. 5.

FIG. 7 is a top view of a portion of the clamp illustrated in FIG. 5.

FIG. 8 is a top view of a portion of another clamp in accordance with a preferred embodiment of a present invention.

FIG. 9 is a side view of a probe support in accordance with one embodiment of a present invention.

FIG. 10 is a section view taken along line 10-10 in FIG. 9.

FIG. 11 is a section view showing a surgical probe component mounted on a clamp member with the probe support illustrated in FIGS. 9 and 10.

FIG. 12 is a side view of a clamp component in accordance with one embodiment of a present invention.

FIG. 13 is a section view taken along line 13-13 in FIG. 12.

FIG. 14 is a section view showing the clamp component illustrated in FIGS. 12 and 13 mounted on a clamp member.

FIG. 15 is a side, partial section view of a clamp component in accordance with one embodiment of a present invention.

FIG. 16 is a section view taken along line 16-16 in FIG. 15.

FIG. 17 is a section view taken along line 17-17 in FIG. 15.

FIG. 18 is a diagrammatic view showing one exemplary manner by which the electrodes and temperature sensors on a dual mode lesion formation apparatus are connected to a pair of electrical connectors.

FIG. 19 is a diagrammatic view showing one exemplary manner by which the electrodes and temperature sensors on another dual mode lesion formation apparatus are connected to a pair of electrical connectors.

DETAILED DESCRIPTION OF THE EXEMPLARY EMBODIMENTS

Figure 20:
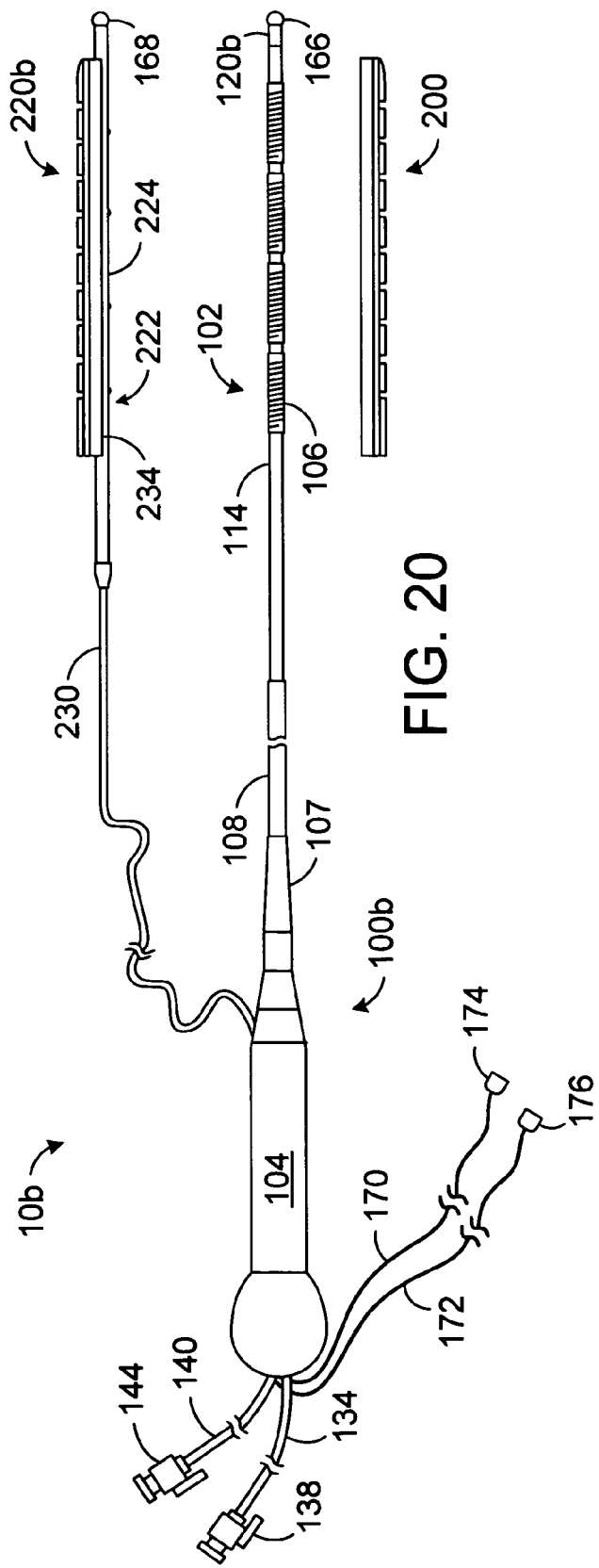
FIG. 20 is a plan view of a dual mode lesion formation apparatus in accordance with one embodiment of a present invention.

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:

I. Introduction
II. Exemplary Dual Mode Lesion Formation Apparatus
III. Exemplary Systems
IV. Exemplary Methods The section titles and overall organization of the present detailed description are for the purpose of convenience only and are not intended to limit the present inventions.

I. Introduction

This specification discloses a number of structures, mainly in the context of cardiac treatment, because the structures are well suited for use with myocardial tissue. Nevertheless, it should be appreciated that the structures are applicable for use in therapies involving other types of soft tissue. For example, various aspects of the present inventions have applications in procedures concerning other regions of the body such as the prostate, liver, brain, gall bladder, uterus, breasts, lungs, and other solid organs.

II. Exemplary Dual Mode Lesion Formation Apparatus

A dual mode lesion formation apparatus in accordance with one embodiment of a present invention is generally represented by reference numeral 10 in FIG. 1. The exemplary dual mode lesion formation apparatus 10 includes a surgical probe component 100, a probe support 200 and a clamp component 220. The probe support 200 is adapted to removably secure the distal portion of the surgical probe component 100 to one clamp member on a conventional clamp, while the clamp component 220 is adapted to be removably secured to the other clamp member. In the "probe" mode of operation, only the surgical probe component 100 will be used. In the "clamp" mode of operation, the surgical probe component 100, probe support 200, and clamp component 220 are removably secured to a conventional clamp so as to convert the clamp into an electrosurgical device that may be used to form lesions in the manner discussed in greater detail in Sections III and IV below. Alternatively, in other implementations, a clamp may be provided with its own probe support and/or clamp component. The electrodes and temperature sensors on the surgical probe component 100 and clamp component 220 may be connected to a pair of electrical connectors in such a manner that one of the electrical connectors will be used to connect to the lesion formation apparatus 10 to an electrosurgical unit ("ESU") during the probe mode of operation and the other electrical connector will be used to connect the lesion formation apparatus to the ESU during the clamp mode of operation, as is discussed in greater detail below with reference to FIGS. 18 and 19.

There are a variety of advantages associated with such a device. By way of example, but not limitation, a large portion of the expense associated with the manufacture of electrosurgical probes and clamps is associated with the electrode and temperature sensor segments of the assembly process. The present inventions significantly reduce these assembly related expenses because the electrodes and temperature sensors on the surgical probe component are used in both the probe mode of operation and the clamp mode of operation, thereby eliminating the need to separately assemble electrodes and temperature sensors on a surgical probe as well as on a separate electrosurgical clamp. The sterilization, packaging and shipment of the present dual mode lesion formation apparatus may also be accomplished in a manner that is more efficient than the sterilization, packaging and shipment of separate devices.

Referring to FIGS. 1-4, the surgical probe component 100 in the exemplary implementation includes a relatively short shaft 102, a handle 104 that is secured to the shaft, and one or more electrodes 106 or other energy transmission elements on the distal portion of the shaft. A strain relief element 107 may also be provided. The shaft 102 is preferably, although not necessarily, about 20 cm to 55 cm in length, and most preferably about 20 cm to 30 cm in length. The shaft 102 is also preferably relatively stiff. In other words, the shaft 102 is rigid, malleable, or somewhat flexible. A rigid shaft cannot be bent. A malleable shaft is a shaft that can be readily bent by the physician to a desired shape, without springing back when released, so that it will remain in that shape during the surgical procedure. Thus, the stiffness of a malleable shaft must be low enough to allow the shaft to be bent, but high enough to resist bending when the forces associated with a surgical procedure are applied to the shaft. A somewhat flexible shaft will bend and spring back when released. However, the force required to bend the shaft must be substantial.

In the exemplary implementation illustrated in FIGS. 1-4, the shaft 102 consists of a proximal portion 108, including a malleable hypotube 110 and a non-conductive outer polymer coating 112, and distal portion 114, including a malleable mandrel 116 and a multi-lumen electrically non-conductive outer structure 118. The proximal portion 108 will typically be about 15 to 40 cm in length, while the distal portion 114 will typically be about 5 to 15 cm in length. The proximal end of the malleable mandrel 116 is secured to the inner surface of the distal end of the hypotube 110 by, for example, soldering, spot welding or adhesives. Mechanical methods, such as crimping and mechanical fasteners, may also be employed. The distal end of the malleable mandrel 116 is secured to a tip member 120. The handle 104 is configured to be gripped by the physician and used to press the shaft distal portion 114 and electrodes 106 against tissue. To that end, the exemplary handle 104 is also about 7 to 18 cm in length and the main portion of the handle is about 2 to 5 cm around its perimeter (measured perpendicularly to the longitudinal axis), which is suitable for gripping by the physician.

The exemplary surgical probe component 100 is a fluid cooled surgical probe and, as illustrated in FIG. 3, the electrically non-conductive outer structure 118 includes fluid inlet and outlet lumens 122 and 124. Power and signal wire lumens 126 and 128, as well as a central lumen 130 for the mandrel 116, are also provided. The tip member 120 includes a connection lumen (not shown) that connects the inlet lumen 122 to the outlet lumen 124, as well as a pair of plugs (not shown) to seal the power and signal wire lumens 126 and 128. Heat from the electrodes 106 is transferred through the outer structure 118 to fluid that is flowing through the inlet and outlet lumens 122 and 124. Accordingly, in addition to being electrically non-conductive, the material used to form the outer structure 118 should be relatively high in thermal conductivity. As used herein, "relatively high" thermal conductivity is at least about 1 W/m·K and preferably ranges from about 1 to about 10 W/m·K. Suitable electrically non-conductive, thermally conductive thermoplastics for the outer structure 118 include flexible thermoplastic polymer materials, such as nylon or polyurethane, which are filled with a filler that promotes heat transfer. Suitable fillers include graphite, aluminum, tungsten and ceramic powders. Another suitable filler is Carborundum CarboTherm™ boron nitride powder manufactured by Saint-Gobain in Cavaillon, France.

In addition to the aforementioned fillers, heat transfer may be promoted by minimizing the thickness of the electrically non-conductive material between the lumens 122 and 124 and the electrodes 106 and by maximizing the cross-sectional area of the inlet and outlet lumens. With respect to the outer structure 118 illustrated in FIG. 3, for example, in an implementation where the outer diameter of the outer structure is about 8 French (2.66 mm), the thickness of the outer wall 132 between the electrodes 106 and the inlet and outlet lumens 122 and 124 will be about 0.08 mm to about 0.36 mm. It should be noted that when the outer wall thickness is about 0.02 mm or less, materials with less than "relatively high" thermal conductivities, such as Pebax® material and polyurethane, may also be used for the outer structure 118.

Suitable materials for the malleable hypotube 110 include annealed stainless steel, while the suitable material for the mandrel 116 includes annealed stainless steel and beryllium copper.

As illustrated for example in FIGS. 1-4, fluid may be supplied to the surgical probe component 100 by way of an infusion tube 134, which is connected to the inlet lumen 122. The infusion tube 134 extends through an aperture 136 in the handle 104 and is provided with stop-cock 138, which may be connected to a fluid supply and control apparatus 400 in the manner described below with reference to FIGS. 21-24. Similarly, a ventilation tube 140 is connected to the outlet lumen 124 and extends through an aperture 142 in the handle 104. The ventilation tube 140 includes a stopcock 144 that may be connected to the fluid supply and control apparatus 400.

The electrodes 106 in the exemplary probe component 100 illustrated in FIGS. 1-4 are electrically coupled to individual power wires 146 that pass from the power wire lumen 126, and through a power wire tube 148, to the handle 104. A plurality of temperature sensors 150, such as thermocouples or thermistors, may be located on, under, abutting the longitudinal end edges of, or in between, the electrodes 106. A reference thermocouple (not shown) may also be provided. In the exemplary implementation, temperature sensors 150 are located at both longitudinal ends of each electrode 106. The temperature sensors 150 are connected to signal wires 152, which pass through the signal wire lumen 128, a signal wire tube 154 and into the handle 104. The temperature sensors 150 are also located within a linear channel 156 that is formed in the non-conductive outer structure 118. The linear channel 156 insures that the temperature sensors will all face in the same direction (e.g. facing tissue) and be arranged in linear fashion. The power and signal wires 146 and 152 are connected to electrical connectors in the handle 104 in the manner described below with reference to FIGS. 18 and 19.

With respect to materials, the electrodes 106 are preferably in the form of wound, spiral closed coils. The coils are made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility. Preferred coil electrodes are disclosed in U.S. Pat. Nos. 5,797,905 and 6,245,068.

Alternatively, the electrodes 106 may be in the form of solid rings of conductive material, like platinum, or can comprise a conductive material, like platinum-iridium or gold, coated upon the device using conventional coating techniques or an ion beam assisted deposition (IBAD) process. For better adherence, an undercoating of nickel, silver or titanium can be applied. The electrodes can also be in the form of helical ribbons. The electrodes can also be formed with a conductive ink compound that is pad printed onto a non-conductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks. Open coil electrodes may also be employed. Still other types of electrodes are formed from electroless plated copper on a polyimide film or tubular substrate. Gold, nickel or silver should be plated over the copper for electrochemical stability and improved biocompatibility. The plating can be applied in continuous form (up to about 1-2 cm in length at most) or can be applied in a pattern that is designed to improve current density distributions and/or electrode flexing characteristics. Temperature sensors (e.g. thermocouples) may be incorporated into the electrode structure by placing the temperature sensors in a channel in the polyimide film or tubular substrate and then plating over them.

The exemplary flexible electrodes 106 are preferably about 4 mm to about 20 mm in length. In the illustrated embodiments, the electrodes 106 are 15 mm in length with 2 mm spacing, which will result in the creation of continuous lesion patterns in tissue when coagulation energy is applied simultaneously to adjacent electrodes. For rigid electrodes, the length of the each electrode can vary from about 2 mm to about 10 mm. Using multiple rigid electrodes longer than about 10 mm each adversely effects the overall flexibility of the device, while electrodes having lengths of less than about 2 mm do not consistently form the desired continuous lesion patterns. Additionally, although the illustrated embodiments include four (4) electrodes, the number of electrodes or other energy transmission elements may be varied to suit particular applications. For example, it may be desirable to provide a seven (7) electrode surgical probe component so that longer lesions can be formed probe mode. The proximal three (3) electrodes would typically not be aligned with the probe support 200 or used in clamp mode.

In some implementations, the electrodes 106 may be covered with a wettable fluid retention element that is saturated with ionic fluid (such as saline) prior to use. Suitable materials for the fluid retention element include biocompatible fabrics commonly used for vascular patches (such as woven Dacron®), open cell foam materials, hydrogels, nanoporous balloon materials (with very slow fluid delivery to the surface), and hydrophilic nanoporous materials. The effective electrical resistivity of the fluid retention element when wetted with 0.9% saline (normal saline) should range from about 1 Ω-cm to about 2000 Ω-cm. A preferred resistivity for epicardial and endocardial procedures is about 1000 Ω-cm.

Other types of energy transmission elements may be carried by the surgical probe component for the purpose of forming lesions in tissue. For example, infrared lasers, focused and unfocused ultrasonic transducers, microwave electrodes, ohmically heated hot wires, and the like may be substituted for the exemplary electrodes 106.

Additional details concerning fluid cooled surgical probes similar to that described above are presented in U.S. Patent App. Pub. No. 2003/0078644, which is entitled "Apparatus for Supporting Diagnostic and Therapeutic Elements in Contact With Tissue Including Dual Lumen Cooling Device" and incorporated herein by reference.

Although the exemplary surgical probe component 100 is an internally cooled, fluid cooled surgical probe, the present inventions are not limited to such probes. Other exemplary surgical probes include, for example, externally cooled, fluid cooled surgical probes such as those illustrated in U.S. Patent App. Pub. No. 2003/0014048, which is entitled "Fluid Cooled Apparatus for Supporting Diagnostic and Therapeutic Elements in Contact with Tissue" and non-cooled surgical probes such as those illustrated in U.S. Pat. Nos. 6,142,994 and 6,645,200. The exemplary surgical probe component 100 may also be replaced with a catheter probe component in those instances where percutaneous access (e.g. access through the femoral vein to a chamber within the heart) is desired. Suitable catheters are disclosed in U.S. Pat. Nos. 6,013,052, 6,203,525, 6,214,002 and 6,241,754. The U.S. patents and published applications mentioned in this paragraph are incorporated herein by reference.

Turning to the exemplary probe support 200, the probe support may be used to removably secure the distal portion of the surgical probe component 100 (or other lesion formation device) onto one of the clamp members of a clamp. As used herein, the term "clamp" includes, but is not limited to, clamps, clips, forceps, hemostats, and any other surgical device that includes a pair of opposable clamp members that hold tissue, at least one of which is movable relative to the other. In some instances, the clamp members are connected to a scissors-like arrangement including a pair of handle supporting arms that are pivotably connected to one another. The clamp members are secured to one end of the arms and the handles are secured to the other end. Certain clamps that are particularly useful in minimally invasive procedures also include a pair of handles and a pair of clamp members. Here, however, the clamp members and handles are not mounted on the opposite ends of the same arm. Instead, the handles are carried by one end of an elongate housing and the clamp members are carried by the other. A suitable mechanical linkage located within the housing causes the clamp members to move relative to one another in response to movement of the handles. The clamp members may be linear or have a predefined curvature that is optimized for a particular surgical procedure or portion thereof. The clamp members may also be rigid or malleable.

One example of a clamp to which the clamp component 200 may be secured is generally represented by reference numeral 300 in FIGS. 5-7. The clamp 300 includes a pair of rigid arms 302 and 304 that are pivotably connected to one another by a pin 306. The proximal ends of the arms 302 and 304 are respectively connected to a pair of handle members 308 and 310, while the distal ends are respectively connected to a pair of clamp members 312 and 314. The clamp members 312 and 314 may be rigid or malleable and, if rigid, may be linear or have a pre-shaped curvature. A locking device 316 locks the clamp in the closed orientation, and prevents the clamp members 312 and 314 from coming any closer to one another than is illustrated in FIG. 5, thereby defining a predetermined spacing between the clamp members. The clamp 300 is also configured for use with a pair of soft, deformable inserts (not shown) that may be removably carried by the clamp members 312 and 314 and allow the clamp to firmly grip a bodily structure without damaging the structure. To that end, the clamp members 312 and 314 each include a slot 318 (FIGS. 6 and 7) that is provided with a sloped inlet area 320 and the inserts include mating structures that are removably friction fit within the slots. The exemplary clamp component 200 may be mounted on one of the clamp members in place of an insert. Additionally, although the inlet areas 320 are located on the proximal portion of the clamp members 312 and 314, they may also be located on the distal portion of the clamp members, as exemplified by the clamp member 312*a* in FIG. 8.

As illustrated for example in FIGS. 9-11, the exemplary probe support 200 includes a base member 202, a slot 204 configured to receive an energy transmission element supporting device, such as the distal portion 114 of the surgical probe component 100, and a connector 206 that mechanically engages a clamp member. The size and shape of the slot 204 will, of course, depend on the size and shape of the structure that it is holding. The distal portion 114 of the surgical probe component 100 is cylindrical in shape and, according, the exemplary slot 204 has a corresponding arcuate cross-sectional shape. The arc is preferably slightly greater than 180 degrees so that the base member 202 will deflect when surgical probe component distal portion 114 is inserted into the slot 204 and then snap back to hold the distal portion in place. So configured, slightly less than one-half (i.e. about 160° of the 360° circumference) of the surface of the electrodes 106 will be exposed when the surgical probe distal portion 114 is held within the slot 204 in the manner illustrated in FIGS. 11 and 22. The exemplary connector 206 is configured to removably mate with the clamp member slot 318 (FIGS. 6, 7 and 11) and, to that end, is provided with a relatively thin portion 208 and a relatively wide portion 210 that together correspond to the shape of the clamp member slot. The connector 206 may also consist of a plurality of spaced members (as shown) or an elongate unitary structure.

The exemplary base member 202 is preferably formed from a soft, resilient, low durometer material that is electrically insulating. Suitable materials include polyurethane, silicone and polyurethane/silicone blends having a hardness of between about 20 Shore D and about 72 Shore D. In the illustrated embodiment, the base member 202 and connector 206 are an integral structure and the connector is formed from the same material as the base member. Alternatively, the base member 202 and connector 206 may be separate structural elements that are secured to one another. Here, the connector 206 would typically be formed from a harder material than the base member 202. The length of the probe support 200 will vary according to the intended application. In the area of cardiovascular treatments, it is anticipated that suitable lengths will range from, but are not limited to, about 4 cm to about 10 cm. In the exemplary implementation, the probe support 200 about 6 cm in length.

It should also be noted that the present inventions are not limited to the exemplary probe support 200 illustrated in FIGS. 9-11. By way of example, probe supports in accordance with the present inventions may include a connector in the form of a longitudinally extending lumen and be configured to slide over a clamp member in manner illustrated in U.S. Pub. App. No. 2003/0158549 A1, which is incorporated herein by reference. Probe supports in accordance with the present inventions may also be a permanent part of the associated clamp. For example, the probe support 200 could be secured to a clamp with adhesive so that it will conveniently be in place when it is desired to secure a probe to the clamp. Probe supports could also molded onto a clamp.

Referring to FIGS. 1, 12 and 13, the clamp component 220 in the exemplary dual mode lesion formation apparatus 10 is configured to removably support one or more temperature sensors 222, such as thermocouples or thermistors, on a clamp member (e.g. the clamp member 314). Although there are four (4) temperature sensors 222 on the exemplary clamp component 220, the actual number may vary to suit particular application. A reference thermocouple (not shown) may also be provided. The temperature sensors 222 may be used to measure the temperature of tissue on the side of a tissue structure opposite the side that is in contact with the electrodes 106 in the manner discussed in Section IV below. With respect to positioning, the temperature sensors 222 may be carried on the clamp component such that they will be aligned with electrodes 106 when the apparatus 10 is mounted on a clamp 300. The temperature sensors 222 may be centered with respect to each electrode, or biased towards the center of the associated clamp member in order to ensure contact with the tissue between the clamp members. In other implementations, eight (8) temperature sensors 222 may provided and arranged such that two temperatures sensors are aligned with each electrode 106.

The temperature sensors 222 in the illustrated embodiment are carried on a tubular structure 224 that includes a linear channel 226. The linear channel 226 insures that the temperature sensors 222 will all face in the same direction (e.g. facing tissue) and be arranged in linear fashion. The temperature sensors 222 are connected to signal wires 228, which pass through the tubular structure 224, a cable 230 (note FIG. 1) and into the handle 104. Preferably, the cable 230 enters the handle 104 just proximally of the strain relief element 107. The signal wires 228 are connected to an electrical connector in the handle 104 in the manner described below with reference to FIGS. 18 and 19. The distal end of the support structure is closed with an tip member 232.

The temperature sensors 222 and tubular structure 224 may be secured to a clamp member in substantially the same manner as the surgical probe distal portion 114 and electrodes 106. To that end, the clamp component 220 is provided with a base member 234, which has a slot 236, and a connector 238. The size and shape of the slot 236 will, of course, depend on the size and shape of the structure that it is holding. The tubular structure 224 is cylindrical in shape and, according, the exemplary slot 236 has a corresponding arcuate cross-sectional shape. The arc is preferably slightly greater than 180 degrees so that the base member 234 will deflect when a probe is inserted into the slot 236 and then snap back to hold the probe in place. So configured, slightly less than one-half (i.e. about 160° of the 360° circumference) of the surface of the tubular structure when it is held within the slot 236. Adhesive may also be used to hold the tubular structure 224 in place. The exemplary connector 238 is configured to removably mate with the clamp member slot 318 (FIGS. 6, 7 and 14) and, to that end, is provided with a relatively thin portion 240 and a relatively wide portion 242 that together correspond to the shape of the clamp member slot. The connector 238 may also consist of a plurality of spaced members (as shown) or an elongate unitary structure.

With respect to dimensions and materials, the tubular structure 224 may be a flexible structure with an outer diameter that is typically between about 1.5 mm and about 3 mm. Suitable support structure materials include, for example, flexible biocompatible thermoplastic tubing such as unbraided Pebax® material, polyethylene, or polyurethane tubing. The exemplary base member 234 is preferably formed from a soft, resilient, low durometer material that is electrically insulating. Suitable materials include polyurethane, silicone and polyurethane/silicone blends having a hardness of between about 20 Shore D and about 72 Shore D. In the illustrated embodiment, the base member 234 and connector 238 are an integral structure and the connector is formed from the same material as the base member. Alternatively, the base member 234 and connector 238 may be separate structural elements that are secured to one another. Here, the connector 238 would typically be formed from a harder material than the base member 234. The length of the base member 234 will vary according to the intended application. In the area of cardiovascular treatments, it is anticipated that suitable lengths will range from, but are not limited to, about 4 cm to about 10 cm. In the exemplary implementation, the base member 234 about 6 cm in length.

It should also be noted that the present inventions are not limited to the exemplary clamp component 220 illustrated in FIGS. 12-14. By way of example, clamp components in accordance with the present inventions may include a connector in the form of a longitudinally extending lumen and be configured to slide over a clamp member in manner illustrated in U.S. Pub. App. No. 2003/0158549 A1. Clamp components in accordance with the present inventions may also be a permanent part of the associated clamp. For example, the clamp component 220 could be secured to a clamp with adhesive so that it will conveniently be in place when it is desired to secure a probe to the clamp and convert the clamp into an electrosurgical device. Temperature sensors (and a suitable support structure) could also molded onto a clamp.

The exemplary dual mode lesion formation apparatus 10 and clamp 300 are preferably configured such that the electrodes 106 will be parallel to, and relatively close to the tubular structure 224 (i.e. a spacing of about 1-10 mm), when the clamp 300 is in the closed orientation. Such an arrangement will allow the lesion formation apparatus and clamp to grip a bodily structure without cutting through the structure. The configuration of the lesion formation apparatus 10 and clamp 300 may, however, vary from application to application to suit particular situations.

Turning to FIGS. 15-17, an exemplary clamp component 220a, which is otherwise identical to the clamp component 220, includes a return electrode 244 and a power wire 246. The four (4) temperature sensors 222 are located near the longitudinal ends of the electrode 244 and at points half-way between the longitudinal mid-point of the electrode 244 and the longitudinal ends of the electrode. The power wire 246 extends through the handle 104 and a cable 437 to a connector 438 in the manner described below with reference to FIGS. 19 and 23. A dual mode lesion formation apparatus 10a with the exemplary clamp component 220a may be operated in bi-polar mode, where energy emitted by the electrodes 106 is returned to the ESU by way of the electrode 244, as discussed below with reference to FIG. 23.

As noted above, the surgical probe component electrodes 106 and temperature sensors 150 and the clamp component temperature sensors 222 on the exemplary dual mode lesion formation apparatus 10 are connected to a pair of electrical connectors in such a manner that one of the connectors will be used to connect to the lesion formation apparatus 10 to an ESU during the probe mode of operation and the other connector will be used to connect the lesion formation apparatus to the ESU during the clamp mode of operation. To that end, and referring first to FIG. 4, the handle 104 in the exemplary embodiment includes first and second electrical connectors 158 and 160, which are accessible through apertures (or ports) 162 and 164. Suitable electrical connectors include PC boards, edge card connectors, subminiature D connectors, ribbon cable connectors, and pin and socket connectors.

Turning to FIG. 18, the power and signal wires 148 and 152 from the electrodes 106 and temperature sensors 150 on the surgical probe component 100 are connected to the electrical connector 158, which is connected to the ESU during the probe mode of operation. The electrical connector 160 will be connected to the ESU during the clamp mode of operation. As such, the power and signal wires 148 and 152 from the electrodes 106 and temperature sensors 150 surgical probe component 100 are also connected to the electrical connector 160, as are the signal wires 228 from the temperature sensors 222 on the clamp component 220. In those instances where the clamp component 220*a* is employed, the power wire 246 from the electrode 244 will also be connected to one of the power return ports on the ESU by the connector 438 in the manner described below with reference to FIG. 23.

In some implementations, each of the electrical connector (e.g. PC boards) 158 and 160 are provided with electronic codes that tell ESU which mode of operation is the desired mode of operation. Accordingly, the electrical connector 158 will include electronic codes indicative of the probe mode and the electrical connector 160 will include electronic codes indicative of the clamp mode.

Dual mode lesion formation apparatus in accordance with the present inventions may also be provided with stimulation electrodes that are used to stimulate tissue (such as by pacing). For example, the exemplary dual mode lesion formation apparatus 10*b* illustrated in FIG. 20 is essentially identical to the lesion formation apparatus 10 illustrated in FIG. 1 and similar elements are represented by similar reference numerals. Here, however, the surgical probe component 100*b* and the clamp component 220*b* are provide with tissue stimulation (or "pacing") electrodes 166 and 168. The stimulation electrodes may be used to perform a variety of functions before, during and after a lesion formation procedure. For example, and as described in greater detail below, the stimulation electrodes may be used to confirm whether or not a therapeutic lesion has been formed after the coagulation energy has been discontinued. Stimulation energy may be used because non-viable tissue (e.g. coagulated tissue) cannot be stimulated and will not propagate stimulation energy to nearby tissue.

The tissue stimulation electrodes 166 and 168, which are respectively carried on the distal ends of the surgical probe component 100*b* and the clamp component 220*b* in the illustrated embodiment, are connected to signal wires 170 and 172. The signal wire 170 extends through the surgical probe component signal wire lumen 128 and signal wire tube 154, as well as through the proximal end of the handle 104, to a connector 174. To that end, the tip member 120*b*, which is otherwise identical to the tip member 120, is modified so that it can support the tissue stimulation electrode 166 and includes an aperture (not shown) that allows the signal wire 170 to pass from the electrode to the signal wire lumen 128. The tissue stimulation electrode 168 is mounted on the distal end of the tubular structure 224 in place of the tip member 232 and the signal wire 172 passes through the tubular structure and the cable 230, as well as through the proximal end of the handle 104, to a connector 176. The connectors 174 and 176 may be connected to a conventional pacing apparatus, or to an ECG machine that is capable of monitoring and recording electrical impulses, as is describe in greater detail in Sections III and IV below.

Minor adjustments (as compared to the dual mode lesion apparatus 10) may also be made so that the tissue stimulation electrodes 166 and 168 will be located distal of the distal ends of the associated clamp members (FIG. 24) when the apparatus 10*b* is used in clamp mode. For example, the electrodes 106 and temperature sensors 222 may be moved proximally so that the tissue stimulation electrodes 166 and 168 will be located distally of the probe support 200 and the base member 234.

Tissue stimulation electrodes 166 and 168 may also be added to the surgical probe 100 and the clamp member 220*a* on the dual mode lesion formation apparatus 10*a*. The resulting dual mode lesion formation apparatus (not shown) would be essentially identical to the apparatus 10*b* but for the use of the clamp member 220*a* and its associated wiring for the electrode 244.

Alternatively, or additionally, tissue stimulation electrodes (not shown) may be provided on a surgical probe component between the electrodes 106, proximal of the proximal-most electrode 106 and distal of the distal-most electrode 106. Such stimulation electrodes may be used to determine the depth of a lesion formed by the electrodes 106 and, correspondingly, whether or not a lesion is transmural at various points along the length of the lesion. Stimulation energy may be used to determine lesion depth because non-viable tissue (e.g. coagulated tissue) cannot be stimulated and will not propagate stimulation energy to nearby tissue. As such, when the application of stimulation energy that should stimulate tissue at a known depth fails to do so, and that depth is greater than or equal to the thickness of the body structure, it may be inferred that a transmural lesion has been formed.

Additional information concerning tissue stimulation electrodes, as well as the manner in which they may be employed in conjunction with a surgical probe and a clamp based device, is provided in U.S. application Ser. No. 10/727,143, which is entitled "Surgical Methods And Apparatus For Forming Lesions In Tissue And Confirming Whether A Therapeutic Lesion Has Been Formed" and incorporated herein by reference.

III. Exemplary Systems

Figure 21:
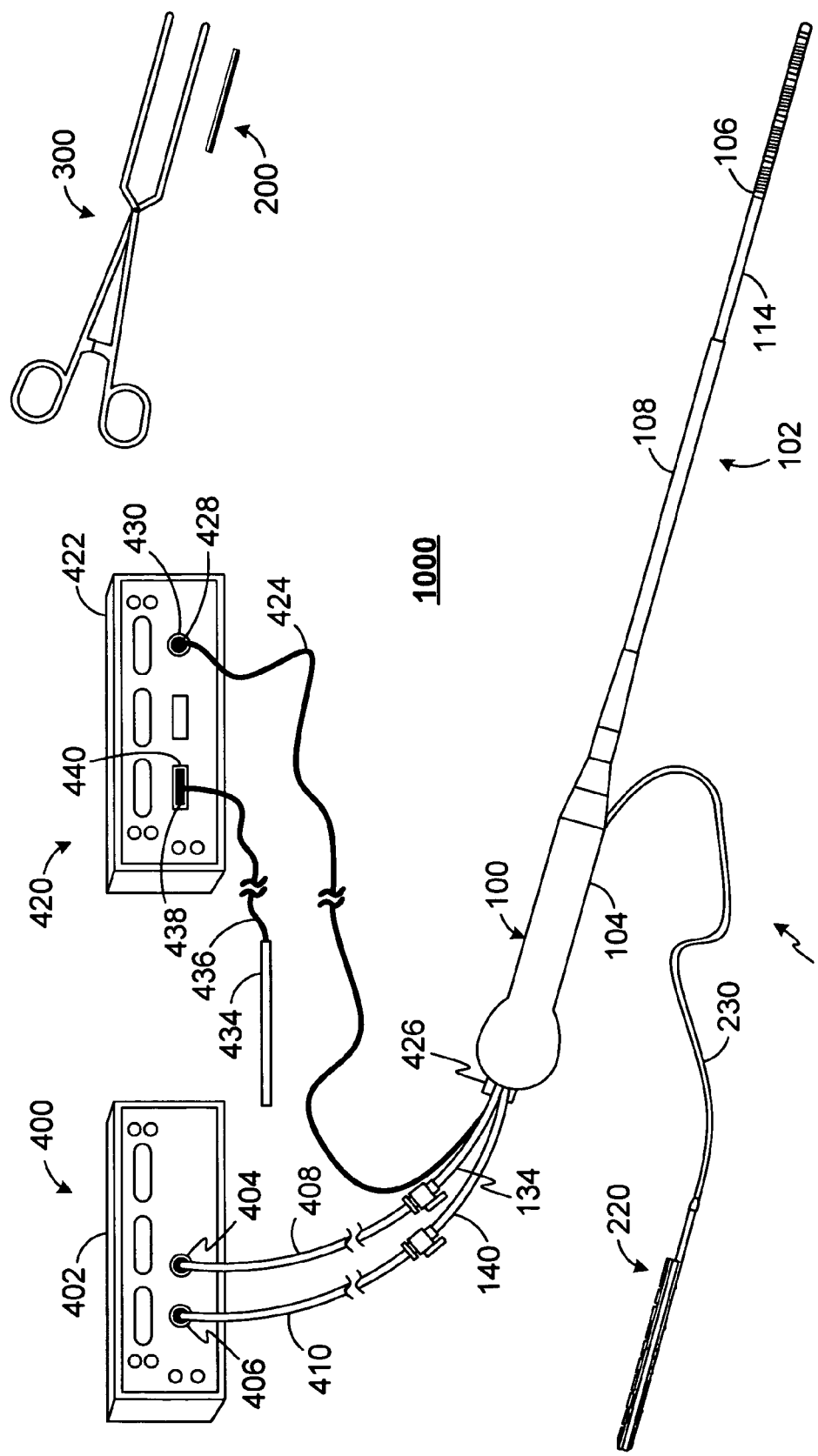
FIG. 21 is a perspective view of a surgical system in accordance with a preferred embodiment of a present invention.
Figure 22:
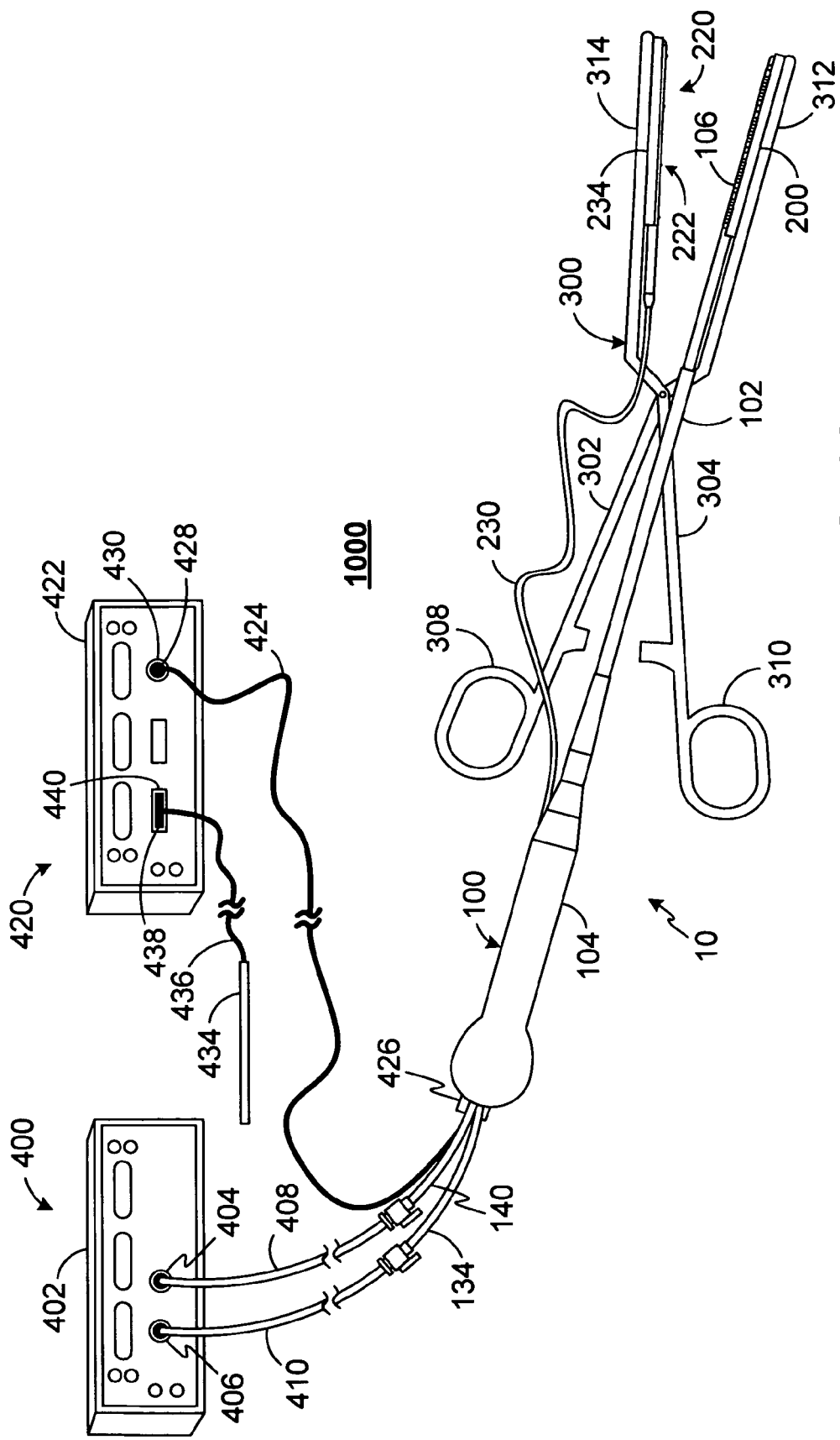
FIG. 22 is a perspective view of a surgical system in accordance with a preferred embodiment of a present invention.

A tissue coagulation system 1000 in accordance with one embodiment of a present invention is illustrated in FIGS. 21 and 22. The exemplary system 1000 includes the dual mode lesion formation apparatus 10, a fluid supply and control apparatus 400 and a power supply and control apparatus 420. The tissue coagulation system 1000 may be operated in probe mode (FIG. 21), where the surgical probe component 100 is used to perform therapeutic operations on tissue and the clamp component 220 is not used. The tissue coagulation system 1000 may also be operated in clamp mode (FIG. 22), where the surgical probe component 100 and clamp component 220 are mounted on the clamp 300 to form a clamp-based tissue coagulation device.

The fluid supply and control apparatus 400, which may be used to supply cooling fluid to the surgical probe component 100, includes housing 402, a fluid outlet port 404, and a fluid inlet port 406. The fluid outlet port 404 may be coupled to the stopcock or other connector associated with the infusion tube 134 (and, therefore, to the inlet lumen 122) by a connector tube 408, while the fluid inlet port 406 may be coupled to the stopcock or other connector associated with the ventilation tube 140 (and, therefore, to the outlet lumen 124) by a connector tube 410. An infusion pump capable of variable flow rates is one example of a suitable fluid supply and control apparatus. The cooling fluid is not limited to any particular fluid. Preferably, however, the fluid will be a low or electrically non-conductive fluid such as sterile water or 0.9% saline solution. A suitable fluid inlet temperature is about 0 to 25° C. and the fluid supply and control apparatus 400 may be provided with a suitable cooling system, if desired, to bring the temperature of the fluid down to the desired level. In a four electrode embodiment where 150 W is being supplied to the electrodes 106, for example, a suitable constant fluid flow rate is about 5 ml/min to about 20 ml/min.

The power supply and control apparatus 420 includes an electrosurgical unit ("ESU") 422 that supplies and controls RF power. A suitable ESU is the Model 4810A ESU sold by Boston Scientific Corporation of Natick, Mass., which is capable of supplying and controlling power on an electrode-by-electrode basis. This is sometimes referred to as "multi-channel control." Typically, power to the surgical probe component 100 will typically be controlled as a function of the temperature at each electrode 106 in order to insure that tissue is coagulated without over-heating and causing coagulum and charring. With respect to temperature sensing at the surgical probe component electrodes 106, temperature is measured by the aforementioned temperatures sensors 150. Alternatively, in those instances where temperature sensors are not employed, the respective temperatures at each electrode 106 may be determined by measuring impedance at each electrode. In either case, the ESU 422 preferably controls power to the electrodes 106 as a function of temperature in both the probe mode of operation and the clamp mode of operation. The temperature of tissue adjacent to the clamp component 220 is measured by the temperature sensors 222.

In addition to the temperatures measured at the electrodes 106, the ESU 422 may also be used to control power to the electrodes as a function of the temperature measured by the clamp component temperature sensors 222 in the clamp mode of operation. An inventor herein has determined that temperature on the side of the target tissue structure opposite an energy transmission element (e.g. the electrodes 106) is indicative of lesion transmurality (i.e. whether or not a lesion that extends from one side of the target tissue structure to the other has been formed). More specifically, the inventor herein has determined that measured temperatures of about 50° C. to about 60° C. on the side of the tissue structure opposite the side that is in contact with surgical probe electrodes 106 for at least 1 second are indicative of the formation of a transmural lesion. The power supply and control apparatus 420 may, therefore, be configured to discontinue energy transmission when a predetermined temperature (e.g. a temperature between about 50° C. and about 60° C.) is measured by the temperature sensors 222 for at least 3 seconds. Alternatively, or in addition, the power supply and control apparatus 420 may also be configured to provide an audible or visible indication that the predetermined temperature has been measured for a predetermined period.

The ESU 422 transmits energy to the electrodes 106 by way of a cable 424. The cable 424 includes a connector 426, which may be individually connected to either the electrical connector 158 (in the probe mode) or the electrical connector 160 (in the clamp mode). As noted above, the surgical probe component power and signal wires 148 and 156 are connected to electrical connector 158 and to electrical connector 160. The clamp component signal wires 228, on the other hand, are only connected to the electrical connector 160. The cable 424 also includes a connector 428, which may be connected to a power output port 430 on the ESU 422.

The power and signal wires 148, 156 and 228 should be connected to the electrical connectors 158 and 160 in such a manner that the physician will know in advance which of the ESU control channels correspond to the four (4) electrodes 106 on the surgical probe component 100 and which of the ESU control channels correspond the four (4) temperature sensors 222 on the clamp component 200. In one exemplary configuration, control channels 1-4 may be used for the surgical probe component electrodes 106 and control channels 5-8 may be used for the four clamp component temperature sensors 222.

The ESU 422 is capable of performing both unipolar and bipolar tissue coagulation procedures in both the probe mode and the clamp mode. During unipolar procedures performed with the exemplary system 1000 illustrated in FIGS. 21 and 22, tissue coagulation energy emitted by the electrodes 106 is returned to the ESU 422 through an indifferent electrode 434 that is externally attached to the skin of the patient with a patch, or one or more electrodes (not shown) that are positioned in the blood pool, and a cable 436. The cable 436 includes a connector 438 that may be connected to one of the power return ports 440 on the ESU 422. Preferably, the ESU power output port 430 and corresponding connector 428 have different configurations than the power return port 440 and corresponding connectors 438 in order to prevent improper connections.

It should also be noted that the tissue coagulation systems 1000-1000*b* may be provided with a suction device that can be secured to the distal portion of the surgical probe component 100 as well as a suction source that can be connected to the suction device. The suction device and suction source may be used to convert surgical probe component 100 into a surgical probe component that has suction capability. The suction prevents the distal portion of surgical probe from moving after the physician has placed it adjacent to the target tissue region. Suitable suction devices and suction sources are described in U.S. Patent Pub. No. 2004/0186467, which is entitled "Apparatus for Maintaining Contact Between Diagnostic and Therapeutic Elements and Tissue and Systems Including the Same" and U.S. application Ser. No. 10/784, 316, which is entitled "Cooled Probes And Apparatus For Maintaining Contact Between Cooled Probes And Tissue," both of which are incorporated herein by reference.

Figure 23:
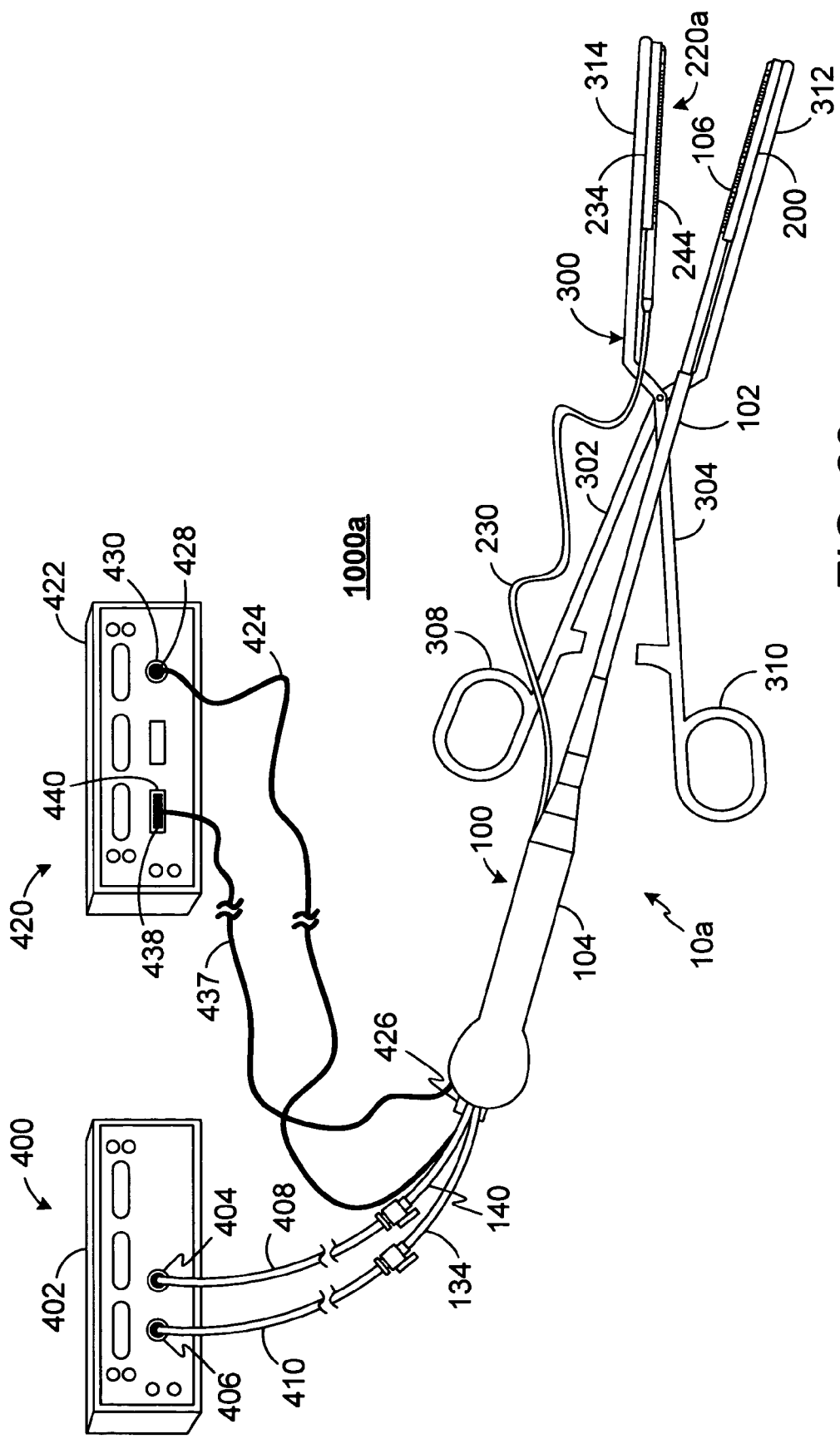
FIG. 23 is a perspective view of a surgical system in accordance with a preferred embodiment of a present invention.

Referring to FIG. 23, bipolar tissue coagulation procedures may also be performed in the clamp mode with the tissue coagulation system 1000*a* illustrated in FIG. 23, which is identical to the system 1000 but for the use of the dual mode lesion formation apparatus 10*a* in place of the dual mode lesion formation apparatus 10. Power transmitted by the electrodes 106 is returned to the ESU 422 by way of the electrode 244 on the clamp component 220*a*.

Figure 24:
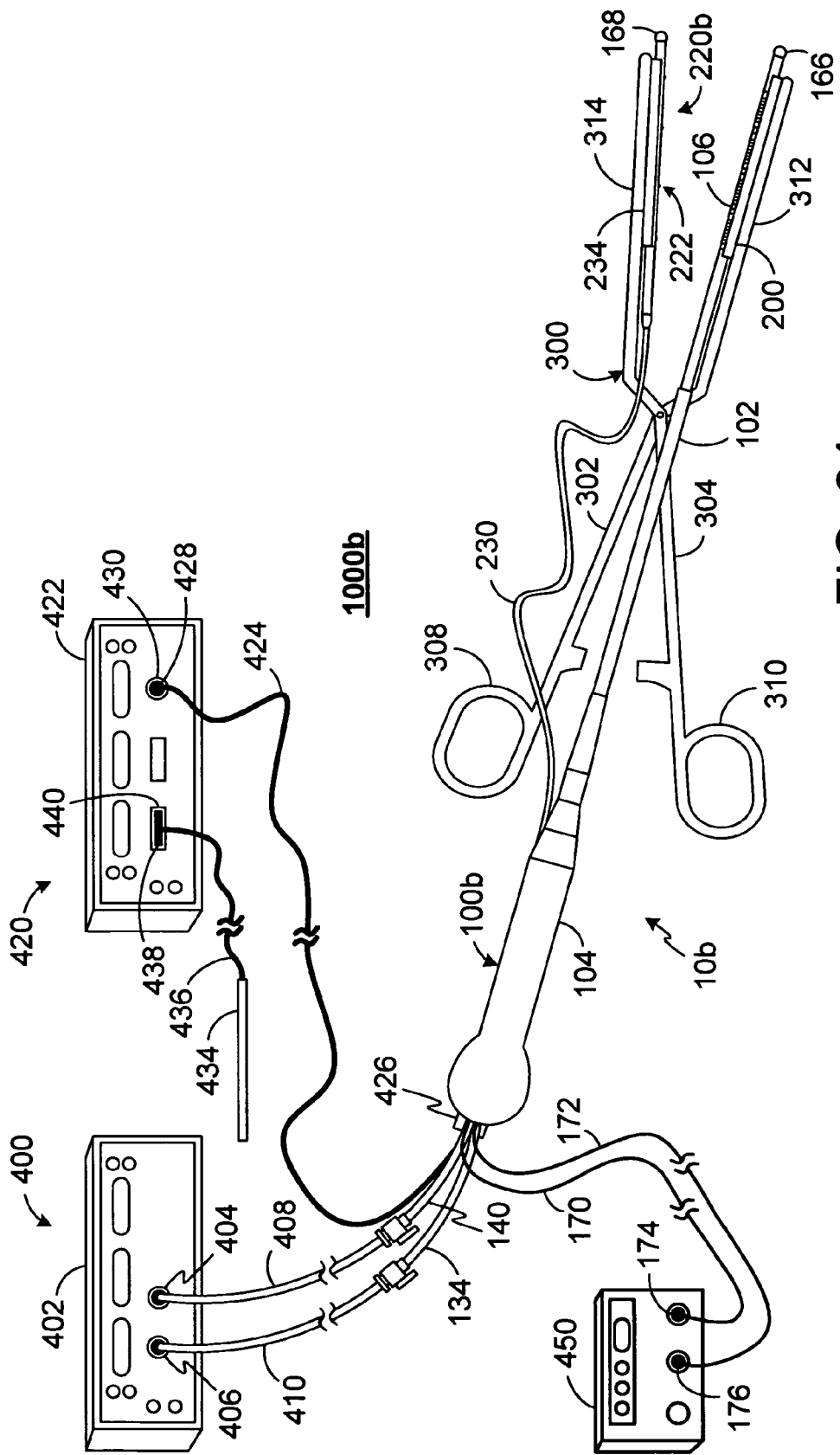
FIG. 24 is a perspective view of a surgical system in accordance with a preferred embodiment of a present invention.

As illustrated for example in FIG. 24, the dual mode lesion formation apparatus 10*b* may employed in a system 1000*b*. The system 1000*b* include the fluid supply and control apparatus 400 and power supply and control apparatus 420, which operate in the manner described above with reference to FIGS. 21 and 22. The exemplary system 1000*b* also includes a pacing apparatus 450 that provides tissue stimulation energy to the electrodes 168 and 170 by way of the signal wires 170 and 172 and connectors 174 and 176. Suitable pacing apparatus include the Medtronic Model Nos. 5330 and 5388 external pulse generators. Alternatively, or in addition, the exemplary system 1000*b* could be provided with an ECG machine that is capable of monitoring and recording electrical impulses from the tissue in contact with the electrodes 168 and 170.

IV. Exemplary Methods

The exemplary tissue coagulation systems 1000-1000*b* illustrated in FIGS. 21-24 may be used to form a variety of lesions in a variety of anatomical structures. By way of example, but not limitation, the tissue coagulation systems 1000-1000*b* may be used in the following manner to form lesions in myocardial tissue to cure atrial fibrillation.

First, the surgical probe component 100 (or 100*b*) may be secured to the one of the clamp members 312 and 314 of the clamp 300 with the probe support 200, the clamp component 220 (or 220*a* or 220*b*) may be secured to the other clamp member, and the dual mode lesion formation apparatus 10 (or 10a or 10b) may be connected to the ESU 422 by way or the clamp mode electrical connector 160. The clamp 300 may then be used to position the probe component distal portion 114 (and, therefore, the electrodes 106 and temperature sensors 150) on left atrial tissue adjacent to one side of the right pulmonary vein pair and to position the clamp component temperature sensors 222 on left atrial tissue adjacent to the opposite side of the right pulmonary vein pair. The clamp members 312 and 314 may then be brought into a completely closed orientation or, depending on the tissue structure, a slightly open orientation so long as the pulmonary veins are firmly held. The ESU 422 is used to supply coagulation energy to one or more of the electrodes 106, and energy is returned to the ESU by way of the indifferent electrode 434 (unipolar mode) or by way of the electrode 244 if the apparatus 10b is employed (bipolar mode). Energy will be continued to be supplied in a controlled manner based on the temperatures monitored by the temperature sensors 150 and 222 until a transmural epicardial lesion around the right pulmonary vein pair is formed (as indicated by the temperature measured at the temperature sensors 222). This process is then repeated on the left pulmonary vein pair and, if necessary, around the left atrial appendage. It should be noted, however, that individual lesions may be formed around each of the pulmonary veins instead of around the pulmonary vein pairs.

The surgical probe component 100 (or 100b) may then be separated from the clamp 300 and the probe support 200, clamp component 220 (or 220a or 220b) and the clamp may be placed on the sterile drape covering the patient, where it can remain until the coagulation procedure is completed.

The surgical probe component 100 (or 100b) may then be used, if necessary, to touch up the aforementioned lesions. If the dual mode lesion formation apparatus 10 (or 10a or 10b) is to be used in probe mode, the ESU 422 will be disconnected from the clamp mode electrical connector 160 and re-connected to the lesion formation apparatus by way of the probe mode electrical connector 158. Tissue coagulation energy from the ESU 422 will be supplied to one, some or all of the electrodes 106 and returned to the ESU by way of the indifferent electrode 434 (unipolar mode) or a non-transmitting electrode 106 (bipolar mode). In addition to touching up lesions, the surgical probe component 100 (or 100b) may be used to create a linear transmural epicardial lesion between the right and left pulmonary vein pairs and/or a linear transmural lesion that extends from the lesion between the right and left pulmonary vein pairs to the left atrial appendage.

Figure 25:
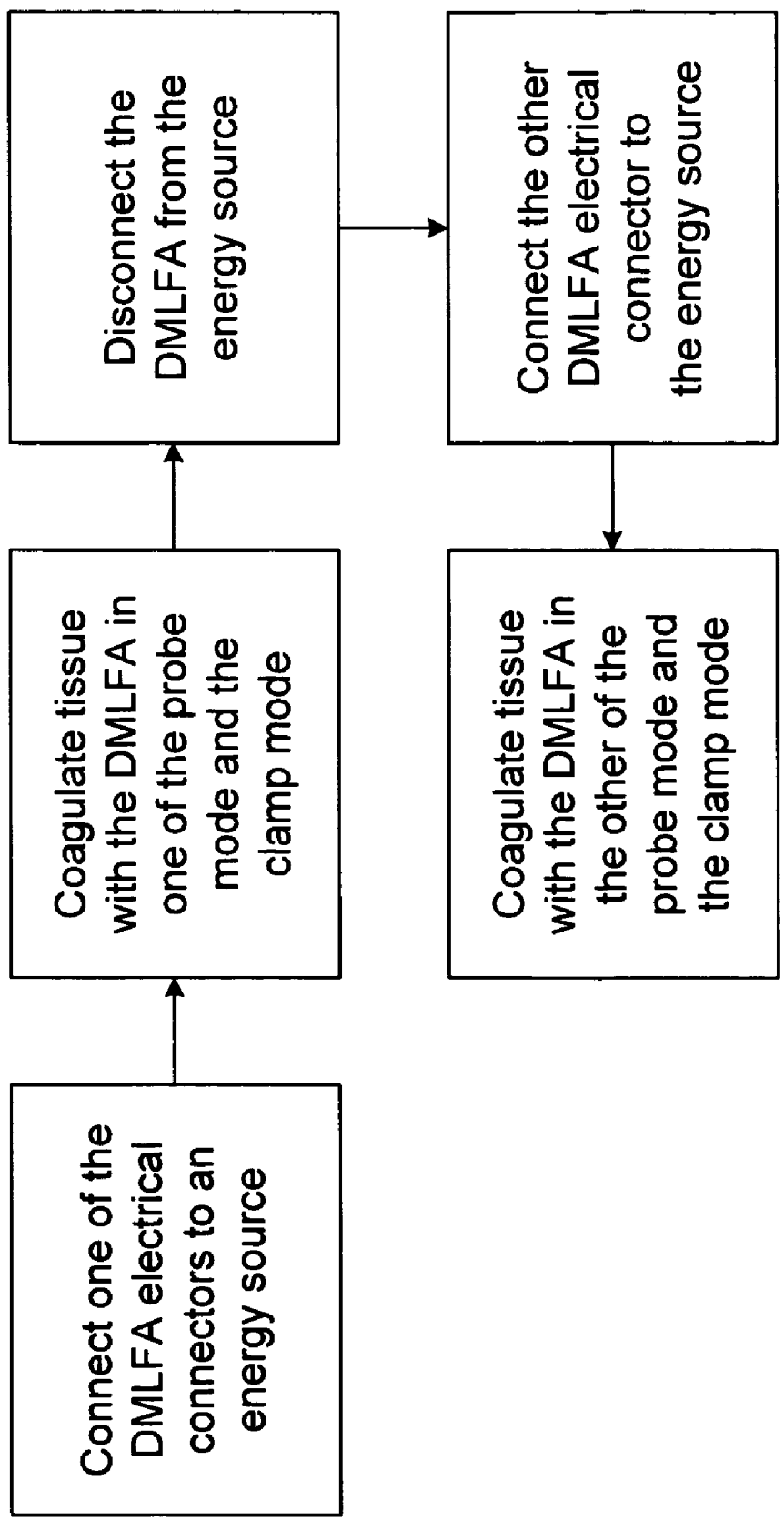
FIG. 25 a flow chart illustrating a method in accordance with one embodiment of a present invention.

The method steps described above are summarized in the flow chart illustrated in FIG. 25 and, in FIG. 25, the dual mode lesion formation apparatus 10-10b are referred to by the abbreviation "DMLFA." It should also be noted that some procedures will require the dual mode lesion formation apparatus 10-10b to be used in the probe mode prior to the clamp mode.

The system 1000b may also be used to determine whether or not a therapeutic lesion (or "complete block") has been formed. For example, the tissue stimulation electrodes 166 and 168 may then be used to supply a bipolar pacing pulse (e.g. about 20 mA) on the side opposite the left atrium of a lesion formed with the dual mode lesion formation apparatus 10b. The physician can determine whether or not a therapeutic lesion has been formed by observing the left atrium. If the pacing pulse is able to cross the lesion, the heart will beat faster (e.g. 120 beats/minute). This may be determined by observation or by use of an ECG machine that is monitoring the heart. Here, additional coagulation will be required to complete the lesion. The failure to stimulate the heart from the side of the lesion opposite the left atrium is, on the other hand, indicative of the formation of a therapeutic lesion. Nevertheless, because muscle bundles are not always connected near the pulmonary veins, it is preferable that the stimulation energy be applied to a number of tissue areas on the side of the lesion opposite the left atrium to reduce the possibility of false negatives. Alternatively, the tissue stimulation electrodes 166 and 168 may be used to monitor tissue within the region that was intended to be isolated. In the context of pulmonary vein isolation, for example, the tissue stimulation electrodes 166 and 168 may be placed in contact with viable tissue on the pulmonary vein side of the lesion.

Although the inventions disclosed herein have been described in terms of the preferred embodiments above, numerous modifications and/or additions to the above-described preferred embodiments would be readily apparent to one skilled in the art. By way of example, but not limitation, the electrical connectors 158 and 160 may be located at the end of one or more cables that extend(s) outwardly from the handle 104, instead of being located within the handle, so that the cable 424 may be eliminated. The inventions includes any combination of the elements from the various species and embodiments disclosed in the specification that are not already described as well as systems that comprise a power supply device (such as an ESU) and/or a fluid supply device and/or a source of simulation energy in combination with any of the apparatus claimed below. It is intended that the scope of the present inventions extend to all such modifications and/or additions and that the scope of the present inventions is limited solely by the claims set forth below.

We claim:

1. A dual mode lesion formation apparatus, comprising:
   a probe component including a handle, a shaft extending from the handle and at least one probe component energy transmission element on the shaft;
   a clamp component tethered to the probe component by an electrical connector, the tethered clamp component being movable relative to the probe component for mounting on a clamp member and including at least one clamp component temperature sensor;
   a first electrical connector operably connected to the at least one probe component energy transmission element; and
   a second electrical connector operably connected to the at least one probe component energy transmission element and to the at least one clamp component temperature sensor.

2. An apparatus as claimed in claim 1, wherein the shaft comprises a relatively short, relatively stiff shaft.

3. An apparatus as claimed in claim 1, wherein the at least one probe component energy transmission element comprises a plurality of spaced energy transmission elements.

4. An apparatus as claimed in claim 1, wherein the at least one probe component includes at least one probe component temperature sensor operably connected to the first and second electrical connectors.

5. An apparatus as claimed in claim 1, wherein the first and second electrical connectors are located at least partially within the handle.

6. An apparatus as claimed in claim 5, wherein the clamp component temperature sensor is connected to the second electrical connector by a signal wire that is located outside the probe component shaft.

7. An apparatus as claimed in claim 1, wherein the clamp component is configured to be removably mounted on the clamp member.

8. An apparatus as claimed in claim 1, wherein the at least one probe component energy transmission element comprises a plurality of probe component energy transmission elements and the at least one clamp component temperature sensor comprises a plurality of clamp component temperature sensors.

9. An apparatus as claimed in claim 1, further comprising:
an electrode carried by the clamp component and operably connected to the second electrical connector.

10. An apparatus as claimed in claim 1, further comprising:
a probe support configured to removably mount a portion of the probe component shaft onto a clamp member.

11. An apparatus as claimed in claim 1, further comprising:
a stimulation electrode carried by one of the probe component and the clamp component.

12. An apparatus as claimed in claim 1, wherein the first and second electrical connectors comprise first and second PC boards.

13. An apparatus as claimed in claim 1, further comprising:
a clamp including first and second clamp members; and
a probe support mounted on the first clamp member and configured to releasably engage the probe component; wherein the clamp component is mounted on the second clamp member.

14. An apparatus as claimed in claim 13, wherein the probe support is removably mounted on the first clamp member and the clamp component is removably mounted on the second clamp member.

15. A lesion formation apparatus for use with a source of tissue coagulation energy, the source of tissue coagulation energy including a power output port, the lesion formation apparatus comprising:
a probe component including a handle, a shaft extending from the handle and a probe component means for transmitting coagulation energy to tissue;
a clamp component tethered to the probe component by an electrical connector, the tethered clamp component being movable relative to the probe component, configured to be mounted on a clamp member and including clamp component means for sensing tissue temperature;
first connector means for facilitating connection of the probe component means for transmitting coagulation energy to the power output port; and
second connector means for facilitating connection of the probe component means for transmitting coagulation energy and the clamp component means for sensing tissue temperature to the power output port.

16. An apparatus as claimed in claim 15, wherein the probe component shaft comprises a relatively short, relatively stiff shaft.

17. An apparatus as claimed in claim 15, wherein the first and second connector means are located at least partially within the handle.

18. An apparatus as claimed in claim 15, wherein the clamp component is configured to be removably mounted on the clamp member.

19. An apparatus as claimed in claim 15, further comprising:
an electrode carried by the clamp component and operably connected to the second connector means.

20. An apparatus as claimed in claim 15, further comprising:
a probe support configured to removably mount a portion of the probe component shaft onto a clamp member.

21. An apparatus as claimed in claim 15, further comprising:
a stimulation electrode carried by one of the probe component and the clamp component.

22. An apparatus as claimed in claim 15, further comprising:
a clamp including first and second clamp members; and
a probe support mounted on the first clamp member and configured to releasably engage the probe component; wherein the clamp component is mounted on the second clamp member.

23. An apparatus as claimed in claim 22, wherein the probe support is removably mounted on the first clamp member and the clamp component is removably mounted on the second clamp member.

24. The apparatus as claimed in claim 1, further comprising the clamp member.

25. The apparatus as claimed in claim 24, further comprising a probe support, the clamp member comprising a first arm, a second arm pivotably connected to the first arm, wherein the clamp component is removably mounted to the first arm, and the probe support is removably mounted to the second arm to removably mount a portion of the probe component shaft onto the clamp member.

26. The apparatus as claimed in claim 1, the probe component energy transmission element being an integral part of the shaft.

27. The apparatus as claimed in claim 1, the clamp component being tethered to the handle of the probe component.

28. The apparatus as claimed in claim 1, wherein the probe component and the clamp component are movable relative to the clamp member, and the clamp component is removably mountable to the clamp member.

29. The apparatus as claimed in claim 1, the electrical connector comprising a flexible cable.

30. The apparatus as claimed in claim 1, wherein the probe component is operable in a first lesion formation mode in which the probe component is utilized independently of the clamp component and the probe component energy transmission element is used to form a lesion, and the clamp member is operable in a second lesion formation mode in which the clamp component mounted to the clamp member and the probe component are utilized together to form a lesion.

* * * * *